(12) United States Patent
Lanphere et al.

(10) Patent No.: US 7,963,287 B2
(45) Date of Patent: Jun. 21, 2011

(54) TISSUE-TREATMENT METHODS

(75) Inventors: Janel Lanphere, Pawtucket, RI (US);
Paul Dicarlo, Middleboro, MA (US);
Steve Anderson, Worcester, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 1729 days.

(21) Appl. No.: 11/117,156

(22) Filed: Apr. 28, 2005

(65) Prior Publication Data
US 2006/0247610 A1 Nov. 2, 2006

(51) Int. Cl.
*A61B 19/00* (2006.01)
(52) U.S. Cl. .............. 128/898; 607/88; 607/89; 607/101
(58) Field of Classification Search .............. 607/88–94, 607/96–107, 115, 133; 606/8, 9, 15; 128/898
See application file for complete search history.

(56) References Cited

U.S. PATENT DOCUMENTS

| | | | |
|---|---|---|---|
| 2,275,154 A | 3/1942 | Merrill et al. |
| 2,609,347 A | 9/1952 | Wilson |
| 3,663,470 A | 5/1972 | Nishimura et al. |
| 3,737,398 A | 6/1973 | Yamaguchi |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,402,319 A | 9/1983 | Handa et al. |
| 4,413,070 A | 11/1983 | Rembaum |
| 4,427,794 A | 1/1984 | Lange et al. |
| 4,428,869 A | 1/1984 | Munteanu et al. |

(Continued)

FOREIGN PATENT DOCUMENTS
AU A-76186/98 10/1998
(Continued)

OTHER PUBLICATIONS

U.S. Appl. No. 10/927,868, filed Aug. 27, 2004, Richard et al.

(Continued)

*Primary Examiner* — Ahmed M Farah
(74) *Attorney, Agent, or Firm* — Fish & Richardson P.C.

(57) ABSTRACT

Polymer insulators and methods of using polymer insulators are disclosed. In some embodiments, a method includes separating a first portion of a subject's tissue from a second portion of the subject's tissue so that there is a space between the first and second portions of tissue. Deionized water, a buffered saline solution, liquid polymers, gels, particles, foams, and/or gases are disposed between the first and second portions of tissue, and the first portion of tissue is exposed to energy to treat the first portion of tissue.

41 Claims, 4 Drawing Sheets

U.S. PATENT DOCUMENTS

| | | | |
|---|---|---|---|
| 4,429,062 A | 1/1984 | Pasztor et al. |
| 4,442,843 A | 4/1984 | Rasor et al. |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor et al. |
| 4,492,720 A | 1/1985 | Moiser |
| 4,515,906 A | 5/1985 | Friesen et al. |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |
| 4,573,967 A | 3/1986 | Hargrove et al. |
| 4,622,362 A | 11/1986 | Rembaum |
| 4,623,706 A | 11/1986 | Timm et al. |
| 4,629,464 A | 12/1986 | Takata et al. |
| 4,640,807 A | 2/1987 | Afghan et al. |
| 4,657,756 A | 4/1987 | Rasor et al. |
| 4,661,137 A | 4/1987 | Garnier et al. |
| 4,663,358 A | 5/1987 | Hyon et al. |
| 4,671,954 A | 6/1987 | Goldberg et al. |
| 4,671,994 A | 6/1987 | Cochran, Jr. |
| 4,674,480 A | 6/1987 | Lemelson |
| 4,675,113 A | 6/1987 | Graves et al. |
| 4,678,710 A | 7/1987 | Sakimoto et al. |
| 4,678,814 A | 7/1987 | Rembaum |
| 4,680,320 A | 7/1987 | Uku et al. |
| 4,681,119 A | 7/1987 | Rasor et al. |
| 4,695,466 A | 9/1987 | Morishita et al. |
| 4,713,076 A | 12/1987 | Draenert |
| 4,742,086 A | 5/1988 | Masamizu et al. |
| 4,743,507 A | 5/1988 | Franses et al. |
| 4,772,635 A | 9/1988 | Mitschker et al. |
| 4,782,097 A | 11/1988 | Jain et al. |
| 4,789,501 A | 12/1988 | Day et al. |
| 4,793,980 A | 12/1988 | Torobin |
| 4,795,741 A | 1/1989 | Leshchiner et al. |
| 4,801,458 A | 1/1989 | Hidaka et al. |
| 4,804,366 A | 2/1989 | Zdeb et al. |
| 4,819,637 A | 4/1989 | Dormandy, Jr. et al. |
| 4,822,535 A | 4/1989 | Ekman et al. |
| 4,833,237 A | 5/1989 | Kawamura et al. |
| 4,850,978 A | 7/1989 | Dudar et al. |
| 4,859,711 A | 8/1989 | Jain et al. |
| 4,863,972 A | 9/1989 | Itagaki et al. |
| 4,889,129 A * | 12/1989 | Dougherty et al. ............ 600/473 |
| 4,897,255 A | 1/1990 | Fritzberg et al. |
| 4,929,400 A | 5/1990 | Rembaum et al. |
| 4,933,372 A | 6/1990 | Feibush et al. |
| 4,946,899 A | 8/1990 | Kennedy et al. |
| 4,954,399 A | 9/1990 | Tani et al. |
| 4,981,625 A | 1/1991 | Rhim et al. |
| 4,990,340 A | 2/1991 | Hidaka et al. |
| 4,999,188 A | 3/1991 | Solodovnik et al. |
| 5,007,940 A | 4/1991 | Berg |
| 5,011,677 A | 4/1991 | Day et al. |
| H915 H | 5/1991 | Gibbs |
| 5,015,423 A | 5/1991 | Eguchi et al. |
| 5,032,117 A | 7/1991 | Motta |
| 5,034,324 A | 7/1991 | Shinozaki et al. |
| 5,047,438 A | 9/1991 | Feibush et al. |
| 5,079,274 A | 1/1992 | Schneider et al. |
| 5,091,205 A | 2/1992 | Fan |
| 5,106,903 A | 4/1992 | Vanderhoff et al. |
| 5,114,421 A | 5/1992 | Polak |
| 5,116,387 A | 5/1992 | Berg |
| 5,120,349 A | 6/1992 | Stewart et al. |
| 5,125,892 A | 6/1992 | Drudik |
| 5,147,631 A | 9/1992 | Glajch et al. |
| 5,147,937 A | 9/1992 | Frazza et al. |
| 5,149,543 A | 9/1992 | Cohen et al. |
| 5,151,096 A * | 9/1992 | Khoury ............................ 606/15 |
| 5,158,573 A | 10/1992 | Berg |
| 5,171,214 A | 12/1992 | Kolber et al. |
| 5,171,217 A | 12/1992 | March et al. |
| 5,181,921 A | 1/1993 | Makita et al. |
| 5,190,760 A | 3/1993 | Baker |
| 5,190,766 A | 3/1993 | Ishihara |
| 5,192,301 A | 3/1993 | Kamiya et al. |
| 5,202,352 A | 4/1993 | Okada et al. |
| 5,216,096 A | 6/1993 | Hattori et al. |
| 5,236,410 A | 8/1993 | Granov et al. |
| 5,253,991 A | 10/1993 | Yokota et al. |
| 5,260,002 A | 11/1993 | Wang |
| 5,262,176 A | 11/1993 | Palmacci et al. |
| 5,263,992 A | 11/1993 | Guire |
| 5,288,763 A | 2/1994 | Li et al. |
| 5,292,814 A | 3/1994 | Bayer et al. |
| 5,302,369 A | 4/1994 | Day et al. |
| 5,314,974 A | 5/1994 | Ito et al. |
| 5,316,774 A | 5/1994 | Eury et al. |
| RE34,640 E | 6/1994 | Kennedy et al. |
| 5,320,639 A | 6/1994 | Rudnick |
| 5,328,936 A | 7/1994 | Leifholtz et al. |
| 5,336,263 A | 8/1994 | Ersek et al. |
| 5,344,452 A | 9/1994 | Lemperle |
| 5,344,867 A | 9/1994 | Morgan et al. |
| 5,354,290 A | 10/1994 | Gross |
| 5,369,133 A | 11/1994 | Ihm et al. |
| 5,369,163 A | 11/1994 | Chiou et al. |
| 5,382,260 A | 1/1995 | Dormandy, Jr. et al. |
| 5,384,124 A | 1/1995 | Courteille et al. |
| 5,397,303 A | 3/1995 | Sancoff et al. |
| 5,398,851 A | 3/1995 | Sancoff et al. |
| 5,403,870 A | 4/1995 | Gross |
| 5,417,982 A | 5/1995 | Modi |
| 5,431,174 A | 7/1995 | Knute |
| 5,435,645 A | 7/1995 | Faccioli et al. |
| 5,441,746 A | 8/1995 | Chagnon |
| 5,443,495 A | 8/1995 | Buscemi et al. |
| 5,456,693 A | 10/1995 | Conston et al. |
| 5,468,801 A | 11/1995 | Antonelli et al. |
| 5,469,854 A | 11/1995 | Unger et al. |
| 5,472,441 A * | 12/1995 | Edwards et al. ................. 606/41 |
| 5,476,472 A | 12/1995 | Dormandy, Jr. et al. |
| 5,484,584 A | 1/1996 | Wallace et al. |
| 5,490,984 A | 2/1996 | Freed |
| 5,494,682 A | 2/1996 | Cohen et al. |
| 5,494,940 A | 2/1996 | Unger et al. |
| 5,512,604 A | 4/1996 | Demopolis |
| 5,514,090 A | 5/1996 | Kriesel et al. |
| 5,525,334 A | 6/1996 | Ito et al. |
| 5,534,589 A | 7/1996 | Hager et al. |
| 5,541,031 A | 7/1996 | Yamashita et al. |
| 5,542,935 A | 8/1996 | Unger et al. |
| 5,553,741 A | 9/1996 | Sancoff et al. |
| 5,556,391 A | 9/1996 | Cercone et al. |
| 5,556,610 A | 9/1996 | Yan et al. |
| 5,558,255 A | 9/1996 | Sancoff et al. |
| 5,558,822 A | 9/1996 | Gitman et al. |
| 5,558,856 A | 9/1996 | Klaveness et al. |
| 5,559,266 A | 9/1996 | Klaveness et al. |
| 5,567,415 A | 10/1996 | Porter |
| 5,569,193 A | 10/1996 | Hofstetter et al. |
| 5,569,449 A | 10/1996 | Klaveness et al. |
| 5,569,468 A | 10/1996 | Modi |
| 5,571,182 A | 11/1996 | Ersek et al. |
| 5,580,575 A | 12/1996 | Unger et al. |
| 5,583,162 A | 12/1996 | Li et al. |
| 5,585,112 A | 12/1996 | Unger et al. |
| 5,595,821 A | 1/1997 | Hager et al. |
| 5,622,657 A | 4/1997 | Takada et al. |
| 5,624,685 A | 4/1997 | Takahashi et al. |
| 5,635,215 A | 6/1997 | Boschetti et al. |
| 5,637,087 A | 6/1997 | O'Neil et al. |
| 5,639,710 A | 6/1997 | Lo et al. |
| 5,648,095 A | 7/1997 | Illum et al. |
| 5,648,100 A | 7/1997 | Boschetti et al. |
| 5,650,116 A | 7/1997 | Thompson |
| 5,651,990 A | 7/1997 | Takada et al. |
| 5,653,922 A | 8/1997 | Li et al. |
| 5,657,756 A | 8/1997 | Vrba |
| 5,681,576 A | 10/1997 | Henry |
| 5,695,480 A | 12/1997 | Evans et al. |
| 5,695,740 A | 12/1997 | Porter |

| Patent No. | Date | Name |
|---|---|---|
| 5,698,271 A | 12/1997 | Liberti et al. |
| 5,701,899 A | 12/1997 | Porter |
| 5,715,824 A | 2/1998 | Unger et al. |
| 5,716,981 A | 2/1998 | Hunter et al. |
| 5,718,884 A | 2/1998 | Klaveness et al. |
| 5,723,269 A | 3/1998 | Akagi et al. |
| 5,725,522 A * | 3/1998 | Sinofsky .................. 606/8 |
| 5,725,534 A | 3/1998 | Rasmussen |
| 5,733,925 A | 3/1998 | Kunz et al. |
| 5,741,331 A | 4/1998 | Pinchuk |
| 5,746,734 A | 5/1998 | Dormandy, Jr. et al. |
| 5,752,974 A | 5/1998 | Rhee et al. |
| 5,756,127 A | 5/1998 | Grisoni et al. |
| 5,760,097 A | 6/1998 | Li et al. |
| 5,766,147 A | 6/1998 | Sancoff et al. |
| 5,770,222 A | 6/1998 | Unger et al. |
| 5,779,668 A | 7/1998 | Grabenkort |
| 5,785,642 A | 7/1998 | Wallace et al. |
| 5,785,682 A | 7/1998 | Grabenkort |
| 5,792,478 A | 8/1998 | Lawin et al. |
| 5,795,562 A | 8/1998 | Klaveness et al. |
| 5,797,953 A | 8/1998 | Tekulve |
| 5,807,323 A | 9/1998 | Kriesel et al. |
| 5,813,411 A | 9/1998 | Van Bladel et al. |
| 5,823,198 A | 10/1998 | Jones et al. |
| 5,827,502 A | 10/1998 | Klaveness et al. |
| 5,827,531 A | 10/1998 | Morrison et al. |
| 5,830,178 A | 11/1998 | Jones et al. |
| 5,833,361 A | 11/1998 | Funk |
| 5,840,387 A | 11/1998 | Berlowitz-Tarrant et al. |
| 5,846,518 A | 12/1998 | Yan et al. |
| 5,853,752 A | 12/1998 | Unger et al. |
| 5,855,615 A | 1/1999 | Bley et al. |
| 5,863,957 A | 1/1999 | Li et al. |
| 5,876,372 A | 3/1999 | Grabenkort et al. |
| 5,877,224 A | 3/1999 | Brocchini et al. |
| 5,885,216 A | 3/1999 | Evans, III et al. |
| 5,885,547 A | 3/1999 | Gray |
| 5,888,546 A | 3/1999 | Ji et al. |
| 5,888,930 A | 3/1999 | Smith et al. |
| 5,891,155 A | 4/1999 | Irie |
| 5,894,022 A | 4/1999 | Ji et al. |
| 5,895,398 A | 4/1999 | Wensel et al. |
| 5,895,411 A | 4/1999 | Irie |
| 5,899,877 A | 5/1999 | Leibitzki et al. |
| 5,902,832 A | 5/1999 | Van Bladel et al. |
| 5,902,834 A | 5/1999 | Porrvik |
| 5,922,025 A | 7/1999 | Hubbard |
| 5,922,304 A | 7/1999 | Unger |
| 5,928,626 A | 7/1999 | Klaveness et al. |
| 5,935,553 A | 8/1999 | Unger et al. |
| 5,951,160 A | 9/1999 | Ronk |
| 5,957,848 A | 9/1999 | Sutton et al. |
| 5,959,073 A | 9/1999 | Schlameus et al. |
| 6,003,566 A | 12/1999 | Thibault et al. |
| 6,015,546 A | 1/2000 | Sutton et al. |
| 6,027,472 A | 2/2000 | Kriesel et al. |
| 6,028,066 A | 2/2000 | Unger |
| 6,047,861 A | 4/2000 | Vidal et al. |
| 6,048,908 A | 4/2000 | Kitagawa |
| 6,051,247 A | 4/2000 | Hench et al. |
| 6,056,721 A | 5/2000 | Shulze |
| 6,056,844 A | 5/2000 | Guiles et al. |
| 6,059,766 A | 5/2000 | Greff |
| 6,063,068 A | 5/2000 | Fowles et al. |
| 6,071,495 A | 6/2000 | Unger et al. |
| 6,071,497 A | 6/2000 | Steiner et al. |
| 6,073,759 A | 6/2000 | Lamborne et al. |
| 6,090,925 A | 7/2000 | Woiszwillo et al. |
| 6,096,344 A | 8/2000 | Liu et al. |
| 6,099,864 A | 8/2000 | Morrison et al. |
| 6,100,306 A | 8/2000 | Li et al. |
| 6,139,963 A | 10/2000 | Fujii et al. |
| 6,149,623 A | 11/2000 | Reynolds |
| 6,160,084 A | 12/2000 | Langer et al. |
| 6,162,377 A | 12/2000 | Ghosh et al. |
| 6,165,193 A | 12/2000 | Greene, Jr. et al. |
| 6,167,313 A | 12/2000 | Gray et al. |
| 6,179,817 B1 | 1/2001 | Zhong |
| 6,191,193 B1 | 2/2001 | Lee et al. |
| 6,214,331 B1 | 4/2001 | Vanderhoff et al. |
| 6,214,384 B1 | 4/2001 | Pallado et al. |
| 6,224,630 B1 | 5/2001 | Bao et al. |
| 6,224,794 B1 | 5/2001 | Amsden et al. |
| 6,235,224 B1 | 5/2001 | Mathiowitz et al. |
| 6,238,403 B1 | 5/2001 | Greene, Jr. et al. |
| 6,245,090 B1 | 6/2001 | Gilson et al. |
| 6,251,661 B1 | 6/2001 | Urabe et al. |
| 6,258,338 B1 | 7/2001 | Gray |
| 6,261,585 B1 | 7/2001 | Sefton et al. |
| 6,264,861 B1 | 7/2001 | Tavernier et al. |
| 6,267,154 B1 | 7/2001 | Felicelli et al. |
| 6,268,053 B1 | 7/2001 | Woiszwillo et al. |
| 6,277,392 B1 | 8/2001 | Klein |
| 6,280,457 B1 | 8/2001 | Wallace et al. |
| 6,291,605 B1 | 9/2001 | Freeman et al. |
| 6,296,604 B1 | 10/2001 | Garibaldi et al. |
| 6,296,622 B1 | 10/2001 | Kurz et al. |
| 6,296,632 B1 | 10/2001 | Luscher et al. |
| 6,306,418 B1 | 10/2001 | Bley |
| 6,306,419 B1 | 10/2001 | Vachon et al. |
| 6,306,425 B1 | 10/2001 | Tice et al. |
| 6,306,427 B1 | 10/2001 | Annonier et al. |
| 6,312,407 B1 | 11/2001 | Zadno-Azizi et al. |
| 6,312,942 B1 | 11/2001 | Plüss-Wenzinger et al. |
| 6,315,709 B1 | 11/2001 | Garibaldi et al. |
| 6,335,384 B1 | 1/2002 | Evans et al. |
| 6,344,182 B1 | 2/2002 | Sutton et al. |
| 6,355,275 B1 | 3/2002 | Klein |
| 6,368,658 B1 | 4/2002 | Schwarz et al. |
| 6,379,373 B1 | 4/2002 | Sawhney et al. |
| 6,388,043 B1 | 5/2002 | Langer et al. |
| 6,394,965 B1 | 5/2002 | Klein |
| 6,410,508 B1 | 6/2002 | Isales et al. |
| 6,423,332 B1 | 7/2002 | Huxel et al. |
| 6,432,437 B1 | 8/2002 | Hubbard |
| 6,436,112 B2 | 8/2002 | Wensel et al. |
| 6,443,941 B1 | 9/2002 | Slepian et al. |
| 6,458,296 B1 | 10/2002 | Heinzen et al. |
| 6,476,069 B2 | 11/2002 | Krall et al. |
| 6,495,155 B1 | 12/2002 | Tice et al. |
| 6,544,503 B1 | 4/2003 | Vanderhoff et al. |
| 6,544,544 B2 | 4/2003 | Hunter et al. |
| 6,545,097 B2 | 4/2003 | Pinchuk et al. |
| 6,547,794 B2 * | 4/2003 | Auge', II .................. 606/86 R |
| 6,565,887 B1 | 5/2003 | Gray et al. |
| 6,575,896 B2 | 6/2003 | Silverman et al. |
| 6,586,364 B2 | 7/2003 | Kubota et al. |
| 6,602,261 B2 | 8/2003 | Greene, Jr. et al. |
| 6,602,524 B2 * | 8/2003 | Batich et al. .................. 424/489 |
| 6,605,111 B2 | 8/2003 | Bose et al. |
| 6,629,947 B1 | 10/2003 | Sahatjian et al. |
| 6,632,531 B2 | 10/2003 | Blankenship |
| 6,652,883 B2 | 11/2003 | Goupil et al. |
| 6,680,046 B1 | 1/2004 | Boschetti |
| 6,699,222 B1 | 3/2004 | Jones et al. |
| 6,706,394 B2 | 3/2004 | Kuehnle et al. |
| 6,899,723 B2 * | 5/2005 | Chen .................. 607/88 |
| 2001/0001835 A1 | 5/2001 | Greene, Jr. et al. |
| 2001/0016210 A1 | 8/2001 | Mathiowitz et al. |
| 2001/0036451 A1 | 11/2001 | Goupil et al. |
| 2001/0051670 A1 | 12/2001 | Goupil et al. |
| 2002/0054912 A1 | 5/2002 | Kim et al. |
| 2002/0061954 A1 | 5/2002 | Davis et al. |
| 2002/0160109 A1 | 10/2002 | Yeo et al. |
| 2002/0182190 A1 | 12/2002 | Naimark et al. |
| 2002/0197208 A1 | 12/2002 | Ruys et al. |
| 2003/0007928 A1 | 1/2003 | Gray |
| 2003/0032935 A1 | 2/2003 | Damiano et al. |
| 2003/0108614 A1 | 6/2003 | Volkonsky et al. |
| 2003/0163187 A1 | 8/2003 | Weber |
| 2003/0183962 A1 | 10/2003 | Buiser et al. |
| 2003/0185895 A1 | 10/2003 | Lanphere et al. |
| 2003/0185896 A1 | 10/2003 | Buiser et al. |
| 2003/0187320 A1 | 10/2003 | Freyman |
| 2003/0194390 A1 | 10/2003 | Krall et al. |
| 2003/0203985 A1 | 10/2003 | Baldwin et al. |
| 2003/0206864 A1 | 11/2003 | Mangin |

| | | | |
|---|---|---|---|
| 2003/0215519 A1 | 11/2003 | Schwarz et al. | |
| 2003/0233150 A1 | 12/2003 | Bourne et al. | |
| 2004/0076582 A1 | 4/2004 | DiMatteo et al. | |
| 2004/0091543 A1 | 5/2004 | Bell et al. | |
| 2004/0092883 A1 | 5/2004 | Casey, III et al. | |
| 2004/0096662 A1 | 5/2004 | Lanphere et al. | |
| 2004/0101564 A1 | 5/2004 | Rioux et al. | |
| 2004/0186377 A1 | 9/2004 | Zhong et al. | |
| 2005/0025800 A1 | 2/2005 | Tan | |
| 2005/0037047 A1 | 2/2005 | Song | |
| 2005/0095428 A1 | 5/2005 | DiCarlo et al. | |
| 2005/0129775 A1 | 6/2005 | Lanphere et al. | |
| 2005/0196449 A1 | 9/2005 | DiCarlo et al. | |
| 2005/0226935 A1 | 10/2005 | Kamath et al. | |
| 2005/0238870 A1 | 10/2005 | Buiser et al. | |
| 2005/0263916 A1 | 12/2005 | Lanphere et al. | |

FOREIGN PATENT DOCUMENTS

| | | |
|---|---|---|
| DE | 3834705 | 4/1990 |
| DE | 42 01 461 | 7/1993 |
| DE | 94 14 868.6 | 12/1994 |
| DE | 297 24 255 U1 | 10/2000 |
| DE | 100 26 620 | 3/2002 |
| EP | 0 067 459 | 12/1982 |
| EP | 0 122 624 | 10/1984 |
| EP | 0 123 235 | 10/1984 |
| EP | 0 243 165 | 10/1987 |
| EP | 0 294 206 | 12/1988 |
| EP | 0 402 031 | 12/1990 |
| EP | 0 422 258 | 4/1991 |
| EP | 0 458 079 | 11/1991 |
| EP | 0 458 745 | 11/1991 |
| EP | 0 470 569 | 2/1992 |
| EP | 0 547 530 | 6/1993 |
| EP | 0 600 529 | 6/1994 |
| EP | 0 623 012 | 11/1994 |
| EP | 0 706 376 | 4/1996 |
| EP | 0 730 847 | 9/1996 |
| EP | 0 744 940 | 12/1996 |
| EP | 0 764 047 | 3/1997 |
| EP | 0 797 988 | 10/1997 |
| EP | 0 993 337 | 4/2000 |
| ES | 2 096 521 | 3/1997 |
| JP | 59-196738 | 11/1984 |
| JP | 62-45637 | 2/1987 |
| JP | 4-74117 | 3/1992 |
| JP | 6-57012 | 3/1994 |
| JP | 9-110678 | 4/1997 |
| JP | 9-165328 | 6/1997 |
| JP | 9-316271 | 12/1997 |
| JP | 10-130329 | 5/1998 |
| JP | 2000189511 | 7/2000 |
| JP | 2001079011 | 3/2001 |
| JP | 2002-017848 | 1/2002 |
| NZ | 255409 | 2/1997 |
| NZ | 517377 | 8/2003 |
| TW | 421658 | 2/2001 |
| WO | WO 91/12823 | 5/1991 |
| WO | WO 92/21327 | 12/1992 |
| WO | WO 93/00063 | 1/1993 |
| WO | WO 93/19702 | 10/1993 |
| WO | WO 94/10936 | 5/1994 |
| WO | WO 95/03036 | 2/1995 |
| WO | WO 95/22318 | 8/1995 |
| WO | WO 95/33553 | 12/1995 |
| WO | WO 96/37165 | 11/1996 |
| WO | WO 96/39464 | 12/1996 |
| WO | WO 98/04616 | 2/1998 |
| WO | WO 98/10798 | 3/1998 |
| WO | WO 98/26737 | 6/1998 |
| WO | WO 98/47532 | 10/1998 |
| WO | WO 99/00187 | 1/1999 |
| WO | WO 99/12577 | 3/1999 |
| WO | WO 99/43380 | 9/1999 |
| WO | WO 99/51278 | 10/1999 |
| WO | WO 99/57176 | 11/1999 |
| WO | WO 00/23054 | 4/2000 |
| WO | WO 00/32112 | 6/2000 |
| WO | WO 00/40259 | 7/2000 |
| WO | WO 00/66183 | 11/2000 |
| WO | WO 00/71196 | 11/2000 |
| WO | WO 00/74633 | 12/2000 |
| WO | WO 01/12359 | 2/2001 |
| WO | WO 01/66016 | 9/2001 |
| WO | WO 01/70291 | 9/2001 |
| WO | WO 01/72281 | 10/2001 |
| WO | WO 01/76845 | 10/2001 |
| WO | WO 01/93920 | 12/2001 |
| WO | WO 02/11696 | 2/2002 |
| WO | WO 02/34298 | 5/2002 |
| WO | WO 02/34299 | 5/2002 |
| WO | WO 02/34300 | 5/2002 |
| WO | WO 02/43580 | 6/2002 |
| WO | WO 03/013552 | 2/2003 |
| WO | WO 03/016364 | 2/2003 |
| WO | WO 03/051451 | 6/2003 |
| WO | WO 03/082359 | 10/2003 |
| WO | WO 2004/019999 | 3/2004 |
| WO | WO 2004/020042 | 3/2004 |
| WO | WO 2004/040972 | 5/2004 |
| WO | WO 2004/073688 | 9/2004 |
| WO | WO 2004/075989 | 9/2004 |

OTHER PUBLICATIONS

U.S. Appl. No. 11/000,741, filed Dec. 1, 2004, Elliott et al.
U.S. Appl. No. 11/070,967, filed Mar. 2, 2005, Anderson et al.
U.S. Appl. No. 11/111,511, filed Apr. 21, 2005, DiCarlo et al.
Abbara et al., "Transcervical Expulsion of a Fibroid as a Result of Uterine Artery Embolization for Leiomyomata", *JVIR*, vol. 10, No. 4, pp. 409-411, 1999.
Abrahams, J.M. et al., "Topic Review: Surface Modifications Enhancing Biological Activity of Guglielmi Detachable Coils in Treating Intracranial Aneurysms", *Surg. Neurol.* 54:34-41, 2000.
Abrahams, J.M. et al., "Delivery of Human Vascular Endothelial Growth Factor with Platinum Coils Enhances Wall Thickening and Coil Impregnation in a Rat Aneurysm Model", *AJNR Am. J. Neuroradiol.* 22:1410-1417, Aug. 2001.
Ahuja, A.A., "Platinum Coil Coatings to Increase Thrombogenicity: A Preliminary Study in Rabbits", *AJNR Am. J. Neuroradiol.* 14:794-798; Jul./Aug. 1993.
Antibody Labeling, http://www.altcorp.com/AffinityLabeling/ablaeling.htm, pp. 1-6, May 20, 2003.
Bachtsi, A.R. et al., "An Experimental Investigation of Enzyme Release from Poly(vinyl alcohol) crosslinked Microspheres", *J. Microencapsulation*, vol. 12, No. 1, pp. 23-35; 1995.
Barr, J.D., et al., "Polyvinyl Alcohol Foam Particles Sizes and Concentrations Injectable through Microcatheters", *JVIR*, vol. 9, No. 1, pp. 113-118; 1998.
Barton, P. et al., "Embolization of Bone Metastases," *Journal of Vascular and Interventional Radiology*, 7(1):81-88 (Jan.-Feb. 1996).
Battinelli, L. et al., "New Class of Poly(vinyl alcohol) Polymrs as Column-Chromatography Stationary Phases for Candida Rugosa Lipase Isoforms Separation", *J. Chromatogr A*, vol. 753, No. 1, pp. 47-55; 1996.
Beaujeux, R. et al., "Trisacryl Gelatin Microspheres for Therapeutic Embolization, II: Preliminary Clinical Evaluation in Tumors and Arteriovenous Malformations," *AJNR Am. J. Neuroradiol.*, 17:541-548, Mar. 1996.
Berenstein, A. et al., "Catheter and Material Selection for Transarterial Embolization: Technical Considerations. II. Materials.", *Radiology*, vol. 132, No. 3, pp. 631-639; 1979.
Berenstein, A. et al., "Microembolization Techniques of Vascular Occlusion: Radiologic, Patohologic, and Clinical Correlation", *AJNR Am I Neuroradiol*, vol. 2, No. 3, pp. 261-267; 1981.
Berkowitz, R.P. et al., "Vaginal Expulsion of Submucosal Fibroids After Uterine Artery Embolization", *Journal of Reproductive Medicine*, vol. 44, No. 4, pp. 373-376; Apr. 1999 http://www.reproductivemedicine.com.
Bourke et al., "Protein Drug Release from Photocrosslinked Poly(vinyl alcohol) Hydrogels," *Society for Biomaterials 28th Annual Meeting Transactions*, p. 144 (2002).

Bradley, E.A. et al., "Transcatheter Uterine Artery Embolisation to Treat Large Uterine Fibroids", *British Journal of Obstetrics and Gynaecology*, vol. 105, pp. 235-240; Feb. 1998.

Brockmann, J. et al., "Radiolabeling of p-Bz-DOTA-CD-11c antibody with [88]Y: Conjugation, Labeling, Biodistribution studies", 2 pages, 2000 http://www.kernchemie.uni-mainz.de/downloads/jb2000/b14_brockmann.pdf.

Bruix, J. et al., "Transarterial Embolization Versus Symptomatic Treatment in Patients With Advanced Hepatocellular Carcinomas: Results of a Randomized, Controlled Trial in a Single Institution", *Hepatology*, Jun. 1998, vol. 27, No. 6, pp. 1578-1583, http://www.hepatitis-central.com/hcv/hcc/embolization/references.html.

Buhle, Jr. EL, "Re: Re: Hepatic Arterial Embolization", *UCLA Medicine Online*, Mar. 10, 1996, http://www.meds.com/archive/mol-cancer/1996/msg00128.html, 2 pages.

Burczak, et al., "Long-term in vivo performance and biocompatibility of poly (vinyl alcohol) hydrogel macrocapsules for hybrid-type artificial pancreas", *Biomaterials*, vol. 17, No. 24, pp. 2351-2356, 1996.

Burczak, et al., "Polymeric materials for biomedical purposes obtained by radiation methods. V. hybrid artificial pancreas", *Polim Med*, vol. 24, No. 1-2, pp. 45-55, 1994 (Summary).

Capozza et al., "Endoscopic treatment of vesico-ureteric reflux and urinary incontinence: technical problems in the paediatric patient," *British Journal of Urology*, 75(4):538-542 (Apr. 1995).

Carroll, B.A. et al., "Microbubbles as Ultrasonic Contrast Agents", *Investigative Radiology*, vol. 14, No. 3, p. 374, Supplement to May-Jun. 1979.

Carroll, B.A. et al., "Gelatin Encapsulated Nitrogen Microbubbles as Ultrasonic Contrast Agents", *Journal of Clinical and Laboratory Research*, vol. 15, No. 1, pp. 260-266, Feb. 1980.

Carstensen, E.L. et al., "Determination of the Acoustic Properties of Blood and its Components", *Journal of Acoustical Society of America*, vol. 25, No. 2, pp. 286-289, Mar. 1953.

Choe, et al., "An experimental study of embolic effect according to infusion rate and concentration of suspension in transarterial particulate embolization", *Invest Radiol*, vol. 32, No. 5, pp. 260-270, 1997.

Chuang et al., "Experimental Canine Hepatic Artery Embolization with Polyvinyl Alcohol Foam Particles", *Departments of Diagnostic Radiology and Veterinary Medicine*, The University of Texas, M.D. Anderson Hospital and Tumor Institute at Houston, Texas, pp. 21-25, Oct. 1982.

Cirkel, U. et al., "Experience with Leuprorelin Acetate Depot in the Treatment of Fibroids: A German Multicentre Study", *Clinical Therapeutics*, vol. 14, Suppl. A, 1992.

Clarian Health Methodist—Indiana Lions Gamma Knife Center, "Arteriovenous Malformation," http://www.clarian.com/tyhealth/gammaknife/cond_arter.asp, 4 pages, Last Updated on Mar. 20, 2000.

Colombo M, "Treatment of Hepatocellular Carcinoma", *Journal of Viral Hepatitis*, 4(Suppl. 1):125-130 (1997), http://home.texoma.net/~moreland/stats/hcc-9.html.

Concentric Medical, Inc.—Product Information (3 pages), 2002.

Cruise et al., "In Vitro and In Vivo Characterization of a Hydrogel-Based Aneurysm Embolization System," *Society for Biomaterials 28th Annual Meeting Transactions*, p. 203 (2002).

Deasy, P. B., "*Microencapsulation and Related Drug Processes*", New York, NY, Marcel Dekker, Inc., 345 pages, 1984 (Table of Contents only).

de Gast, A.N. et al., "Transforming Growth Factor β-coated Platinum Coils for Endovascular Treatment of Aneurysms: An Animal Study", *Neurosurgery*, vol. 49, No. 3, pp. 690-696, Sep. 2001.

Derdeyn, et al., "Collagen-coated acrylic microspheres for embolotherapy: in vivo and in vitro characteristics", *American Journal of Neuroradiology*, vol. 18, No. 4, pp. 647-653, 1997.

Derdeyn, et al., "Polyvinyl alcohol particle size and suspension characteristics", *American Journal of Neuroradiology*, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", *Journal of Pharmaceutical Sciences*, vol. 83, No. 1, pp. 104-106, Jan. 1994.

Duckwiler et al., "Catheters, embolic agents spark neurointervention," *Diagnostic Imaging*, 16(5):66-72 (May 1994).

Ersek et al., "Bioplastique: A New Textured Copolymer Microparticle Promises Permanence in Soft-Tissue Augmentation," *Plastic and Reconstructive Surgery*, 87(4):693-702 (Apr. 1991).

Eskridge, "Interventional Neuroradiology," *Radiology*, 172:991-1006 (Nov. 1989).

Feldman, L. et al., "Transcatheter Vessel Occlusion: Angiographic Results Versus Clinical Success", *Radiology*, vol. 147, pp. 1-5, Apr. 1983.

Ferrofluids, Physical Properties and Applications Ferrofluidics Corp., Nashua, NH, 5 pages, 1986.

FeRx Incorporated, FERX Profile http://www.biotechshares.com/FERX.htm, 4 pages (Retrieved from the internet on Jun. 26, 2003).

"Fibroid Treatment Collective—Fibroid Embolization," 2 pages, http://www.fibroids.org.

Fritzsch, T. et al., "SH U 508, A Transpulmonary Echocontrast Agent", *Investigative Radiology*, vol. 25, Supplement 1, pp. S160-S161, Sep. 1990.

Fujimoto, S. et al., "Biodegradable Mitomycin C Microspheres Given Intra-Arterially for Inoperable Hepatic Cancer", *Cancer*, vol. 56, pp. 2404-2410, 1985.

Gander, et al., "Effect of polymeric network structure on drug release from cross-linked poly(vinyl alcohol) micromatrices", *Pharm Res*, vol. 6, No. 7, pp. 578-584, 1989.

Germano, et al., "Histopathological follow-up study of 66 cerebral arteriovenous malformations after therapeutic embolization with polyvinyl alcohol", *J Neurosurg*, vol. 76, No. 4, pp. 607-614, 1992.

Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, vol. 11, No. 10, pp. 1244-1255, Dec. 2000.

Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.

Gohel, et al., "Formulation design and optimization of modified-release microspheres of diclofenac sodium", *Drug Dev Ind Pharm*, vol. 25, No. 2, pp. 247-251, 1999.

Goldberg, B.B., "Ultrasonic Cholangiography", *Radiology*, vol. 118, pp. 401-404, Feb. 1976.

Goodwin, et al., "Overview of embolic agents and their indications", *Eleventh Annual International Symposium on Endovascular Therapy*, pp. 303-306, 1999.

Goodwin, et al., "Preliminary experience with uterine artery embolization for uterine fibroids", *Journal of Vascular and Interventional Radiology*, vol. 8, No. 4, pp. 517-526, 1997.

Gramiak et al., "Echocardiography of the Aortic Root," *Investigative Radiology*, 3(5):356-366 (Sep.-Oct. 1968).

Gramiak, R. et al., "Ultrasound Cardiography: Contrast Studies in Anatomy and Function", *Radiology*, vol. 92, No. 5, pp. 939-948, Apr. 1969.

Grandfils, et al., "Preparation of poly (D,L) lactide microspheres by emulsion solvent evaporation, and their clinical implications as a convenient embolic material", *J Biomed Mater Res*, vol. 26, No. 4, pp. 467-479, 1992.

Greenwood, L.H. et al., "Obstetric and Nonmalignant Gynecologic Bleeding: Treatment with Angiographic Embolization", *Radiology*, vol. 164, No. 1, pp. 155-159, Jul. 1987.

Gupta et al., "Plasma-induced graft polymerization of acrylic acid onto poly(ethylene terephthalate) films: characterization and human smooth muscle cell growth on grafted films," *Biomaterials*, 23:863-871 (2002).

Halstenberg et al., "Biologically Engineered Protein-*graft*-Poly(ethylene glycol) Hydrogels: A Cell Adhesive and Plasinin-Degradable Biosynthetic Material for Tissue Repair," *Biomacromolecules*, 3(4):710-723 (2002).

Hamada et al., "Embolization with Cellulose Porous Beads, II: Clinical Trial," *AJNR Am. J. Neuroradiol.*, 17:1901-1906 (Nov. 1996).

Hirano et al., "Transcutaneous Intrafold Injection for Unilateral Vocal Fold Paralysis: Functional Results," *Ann. Otol. Rhinol. Laryngol.*, 99(8):598-604 (Aug. 1990).

Horak et al., "Hydrogels in endovascular embolization. I. Spherical particles of poly (2-hydroxyethyl methacrylate) and their medico-biological properties", *Biomaterials*, 7(3):188-192 (May 1986).

Horak et al., "Hydrogels in endovascular embolization. II. Clinical use of spherical particles", *Biomaterials*, 7(6):467-470 (Nov. 1986).

Huang, et al., "Percutaneous endovascular embolization of intracerebral arteriovenous malformations. Experience in 72 cases", *Chin Med J*, vol. 108, No. 6, pp. 413-419, 1995.

"Injectable Tissue Implant Could Repair Ravages of Surgery", Clemson University, Biotech Week, Oct. 22, 2003, p. 117.

Jack, et al., "Radiolabeled polyvinyl alcohol particles: a potential agent to monitor embolization procedures", *Int J Rad Appl Instrum B*, vol. 13, No. 3, pp. 235-243, 1986.

Jiaqi, Y. et al., "A New Embolic Material: Super Absorbent Polymer (SAP) Microsphere and Its Embolic Effects," *Nippon Acta Radiologica*, 56:19-24 (1996) (Abstract).

Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385-398, Feb. 2001, www.iop.org/Journals/pb.

Joy C, et al., "Use of Preoperative Embolization in the Treatment of Vascular Metastatic Lesions of the Spine," http://www.aaos.org/wordhtml/anmeet91/scipro/ppr472.htm, Mar. 12, 1991.

Jung et al., "Sulfobutylated poly(vinyl alcohol)-graft-poly(lactide-co-glycolide)s facilitate the preparation of small negatively charged biodegradable nanospheres," *Journal of Controlled Release*, 67:157-169 (2000).

Kai, et al., "The utility of the microcrystalline cellulose sphere as a particulate embolic agent: an experimental study", *American Journal of Radiology*, vol. 21, No. 6, pp. 1160-1163, 2000.

Kallmes, D.F. et al., "In Vitro Proliferation and Adhesion of Basic Fibroblast Growth Factor-producing Fibroblasts on Platinum Coils", *Radiology*, vol. 206, No. 1, pp. 237-243, Jan. 1998.

Kan, et al., "In vivo microscopy of the liver after injection of lipiodol into the hepatic artery and portal vein in the rat", *Acta Radiologica*, vol. 30, pp. 419-425, 1989.

Kerber, C., "Balloon Catheter with a Calibrated Leak", *Radiology*, vol. 120, pp. 547-550, Sep. 1976.

Kerber et al., "Polyvinyl Alcohol Foam: Prepackaged Emboli for Therapeutic Embolization", *American Journal Roentgenol*, vol. 130, pp. 1193-1194, Jun. 1978.

Kerber, "Flow-Controlled Therapeutic Embolization: A Physiologic and Safe Technique", *AJR*, vol. 134, pp. 557-561, Mar. 1980.

Khankan et al., "Embolic Effects of Superabsorbent Polymer Microspheres in Rabbit Renal Model: Comparison with Tris-acryl Gelatin Microspheres and Polyvinyl Alcohol," *Radiation Medicine*, 22(6):384-390 (2004).

Kim, et al., "Composite poly(vinyl alcohol) beads for controlled drug delivery", *Pharm Res*, vol. 9. No. 1, pp. 10-16, 1992.

Kim et al., "Hollow Silica Spheres of Controlled Size and Porosity by Sol-Gel Processing," *J. Am. Ceram. Soc.*, 74(8):1987-1992 (Aug. 1991).

Kim et al., "Poly(vinyl alcohol) beads with core-shell structure for drug delivery," *Cosmetic and Pharmaceutical Applications of Polymers*, Plenum Press, New York, pp. 209-214 (1991).

Kim et al., "Suspension polymerized poly(vinyl alcohol) beads for drug delivery," *Polymeric Materials: Science and Engineering, Proceedings of the ACS Division of Polymeric Materials: Science and Engineering*, 63:64-67 (1990).

Kochan, J.P. et al., "Interventional Neuroradiology: Current Practices and Techniques at Temple University Hospital," http://www.temple.edu/radiology/stroke.html, 5 pages.

Krinick et al., "A polymeric drug delivery system for the simultaneous delivery of drugs activatable by enzymes and/or light," *J. Biomater. Sci. Polymer Edn*, 5(4):303-324 (1994).

Kuhn, R. et al., "Embolic Occlusion of the Blood Supply to Uterine Myomas: Report of 2 Cases", *Aust. NZ. J. Obstet. Gynaecol.*, vol. 39, No. 1, pp. 120-122, Feb. 1999.

Kurata, et al., "Preoperative embolization for meningiomas using PVA particles", *No Shinkei Geka*, vol. 20, No. 4, pp. 367-373, 1992 (Abstract).

Kurbatova, G.T. et al., "Magnetically-guided Anesthetics Based on Highly Dispersed Iron Powders Coated by Polyacrylamide", *Biofizika*, vol. 47, No. 2, pp. 331-337, Mar.-Apr. 2002 http://intapp.medscape.com/px/medlineapp (Abstract).

Kurosaki et al., "Evaluation of PVA-Gel Spheres as GI-Transit Time Controlling Oral Drug Delivery System", *Proceedings of the 19th International Symposium on Controlled Release of Bioactive Materials*, Orlando, Florida, pp. 273-274, Jul. 26-31, 1992.

Kusano, et al., "Low-dose particulate polyvinylalcohol embolization in massive small artery intenstinal hemorrahage. Experimental and clinical results", *Invest Radiol*, vol. 22, No. 5, pp. 388-392, 1987.

Labarre et al., "Complement activation by substituted polyacrylamide hydrogels for embolisation and implantation", *Biomaterials*, vol. 23, pp. 2319-2327, 2002.

Lammer, et al., "Transcatheteral embolization with polyvinyl alcohol—technic and experimental studies", *Rontgenblatter*, vol. 36, No. 1, pp. 10-14, 1983 (Abstract).

Latchaw et al., "Polyvinyl Foam Embolization of Vascular and Neoplastic Lesions of the Head, Neck, and Spine", *Radiology*, vol. 131, pp. 669-679, Jun. 1979.

Laurent, "Materials and biomaterials for interventional radiology," *Biomed. & Pharmacother.*, 52:76-88 (1998).

Lemperle et al., "PMMA Microspheres for Intradermal Implantation: Part I. Animal Research," *Annals of Plastic Surgery*, 26(1):56-63 (Jan. 1991).

Lendlein, A. et al., "Biodegradable, Elastic Shape-Memory Polymers for Potential Biomedical Applications", *Science*, vol. 296, pp. 1673-1676, May 31, 2002.

Leung et al., "Determinants of Postembolization Syndrome after Hepatic Chemoembolization", *Journal of Vascular and Interventional Radiology*, vol. 12, No. 3, pp. 320-326, Mar. 2001.

Leventon, William, "Hemocompatible Coatings for Blood-Contacting Devices", *Medical Device & Diagnostic Industry: Coating Technologies—New Methods to Ensure Blood Compatibility*, vol. 25, No. 8, pp. 62-67, Aug. 2003.

Levy et al., "Transcatheter Uterine Artery Embolization for the Treatment of Symptomatic Uterine Fibroid Tumors," *Journal of Women's Imaging*, 2(4):168-175 (2000).

Lipman, "Uterine artery embolization for the treatment of symptomatic uterine fibroids: A review," *Applied Radiology*, 29(7):15-20 (Jul. 2000).

Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.

Markoff, et al., "Uterine arteriovenous malformation successfully embolized with a liquid polymer, isobutyl 2-cyanoacrylate", *Am. J. Obstet. Gynecol.*, 155:659-660 (Sep. 1986).

Markus et al., "Experimental Aspects of High-Intensity Transient Signals in the Detection of Emboli," *J. Clin. Ultrasound.*, 23(2):81-87 (Feb. 1995).

Maruhashi, "Modified Polyvinyl Alcohols I and II," *Polyvinyl Alcohol—Developments*, John Wiley & Sons, Chichester, England, pp. 160-161 and pp. 186-191 (1992).

Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J. Neuroradiol.*, vol. 22, pp. 323-333, Feb. 2001.

Mather, P.T., Research Group Homepage, Basic Goals and Methods, http://www.ims.uconn.edu/~mather, 4 pages.

Matsumaru, et al., "Embolic materials for endovascular treatment of cerebral lesions", *J Biomater Sci Polym Ed*, vol. 8, No. 7, pp. 555-569, 1997.

Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", *Neurosurgery*, vol. 53, No. 2, pp. 402-408; Aug. 2003.

Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.

Mavligit, G. et al., "Gastrointestinal Leiomyosarcoma Metastatic to the Liver," *Cancer*, 75(8):2083-2088 (Apr. 15, 1995).

McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.

MerocelXL Sponge with Hytrol http://www.xomed.com/newproducts/merocelxl/merocelxl_earwick.asp, 3 pages, 2001.

Mid-America Interventional Radiological Society, "New Treatment for Uterine Fibroids Avoids Surgery," http://www.mirs.org/fibroids.htm, 6 pages, Submitted in Oct. 1999.

Moroz, P. et al., "Arterial Embolization Hyperthermia in Porcine Renal Tissue", *Journal of Surgical Research*, vol. 105, No. 2, pp. 209-214, Jun. 15, 2002.

Moroz, P. et al., "Hepatic Clearance of Arterially Infused Ferromagnetic Particles", *Int. J. Hyperthermia*, vol. 19, No. 1, pp. 23-24, Feb. 2003, http://www.tandf.co.uk/journals.

Nakabayashi, et al., "Evaluation of particulate embolic materials with MR imaging, scanning electron microscopy, and phase-contrast microscopy", *American Journal of Neuroradiology*, vol. 18, No. 3, pp. 485-491, 1997.

Nakstad, et al., "Embolization of intracranial arteriovenous malformations and fistulas with polyvinyl alcohol particles and platinum fibre coils", *Neuroradiology*, vol. 34, No. 4, pp. 348-351, 1992.

Namiki, "Application of Teflon Paste for Urinary Incontinence—Report of 2 Cases," *Uro. Int.*, 39:280-282 (1984).

Nash, et al., "Modifications of polystyrenic matrices for the purification of proteins. II. Effect of the degree of glutaraldehyde-poly(vinyl alcohol) crosslinking on various dye ligand chromatography systems", *J Chromatogr A*, vol. 776, No. 1, pp. 55-63, 1997.

Nikishin LF et al., "Interventional radiology in diffuse toxic goiter", *European Congress of Radiology*, Abstract 9041, 1999, http://www.ecr.org/conferences/ecr1999/sciprg/abs/p090041.htm, 7 pages.

Ophir, et al., "Ultrasonic backscatter from contrast producing collagen microspheres", *Ultrasonic Imaging*, vol. 2, pp. 67-77, 1980.

Oregon Health Sciences University, "Fibroid Embolization," http://www.uhmc.edu/dotter-fibroid, 34 pages.

Orienti et al., "Crosslinked Polyvinylalcohol Hydrogels as Vehicles for Hydrophilic Drugs," *Arch. Pharm. Pharm. Med. Chem.*, 333:421-424 (2000).

Orsini, L. F. et al., "Pelvic Organs in Premenarcheal Girls: Real-Time Ultrasonography", *Radiology*, vol. 153, No. 1, pp. 113-116, Oct. 1984.

Parker, et al., "A particulate contrast agent with potential for ultrasound imaging of liver", *Ultrasound in Medicine and Biology*, vol. 13, No. 9, pp. 555-566, 1987.

Pedley et al., "Hydrogels in Biomedical Applications," *British Polymer Journal*, 12:99-110 (Sep. 1980).

Pesant A.C. et al., "Dural fistulas involving the cavernous sinus: Treatment by embolization—7 cases", *European Congress of Radiology*, Abstract 3-088, 1997, http://www.ecr.org/conferences/ecr1997/scriprg/abs/9703088p.htm, 1 page.

Phillips, D. R. et al., "Experience with Laparoscopic Leiomyoma Coagulation and Concomitant Operative Hysteroscopy", *J. Am. Assoc. Gynecol. Laparosc*, vol. 4, No. 4, pp. 425-533, Aug. 1997.

Physicians' Desk Reference Family Guide to Women's Health, "Chapter 7—Common Disorders of the Reproductive System," http://www.healthsquare.com/pdrfg/wh/chapters/wh1ch01.htm, 24 pages.

Pistel et al., "Brush-like branched biodegradable polyesters, part III Protein release from microspheres of poly(vinyl alcohol)-graft-poly(D,L-lactic-co-glycolic acid)," *Journal of Controlled Release*, 73:7-20 (2001).

Politano et al., "Periurethral Teflon Injection for Urinary Incontinence," *The Journal of Urology*, 111:180-183 (1974).

Poppe, W. et al., "Pregnancy after Transcatheter Embolization of a Uterine Arteriovenous Malformation", *Am. J. Obstet. Gynecol.*, vol. 156, No. 5, pp. 1179-1180, May 1987.

Pritchard, et al., "Poly(Vinyl Alcohol): Basic Properties and Uses", London, England: Gordon and Breach Science Publishers, pp. 95-97, 1970.

Progelhof et al., "Table 4.21. Properties of electrical insulating films (101)," *Polymer Engineering Principles: Properties, Processes, and Tests for Design*, Hanser Publishers, Munich, p. 383 (1993).

Pryor J. and Berenstein A., "Epistaxis (Nose-bleeds)," http://www.wehealny.org/inn/Radiology/nosebleeds.html, 1 page.

"Pulmonary artery pseudoaneurysm/aneurysm," http://www.mamc.amedd.army.mil/williams/chest/vascular/paaneurysm/paaneyrysm.htm, 2 pages.

Purdy, et al., "Arteriovenous malformations of the brain: choosing embolic materials to enhance safety and ease of excision", *J Neurosurg*, vol. 77, No. 2, pp. 217-222, 1992.

PVA Plus, AngioDynamics® Inc., "Reliable PVA Foam Formulated for Consistency and Controlled Delivery—Embolization Particles Ordering Information," www.angiodynamics.com, 2 pages (Aug. 2002).

Quisling, et al., "Histopathology analysis of intraarterial polyvinyl alcohol microemboli in rat cerebral cortex", *American Journal of Neuroradiology*, vol. 5, pp. 101-104, 1984.

Rajan et al., "Sarcomas Metastatic to the Liver: Response and Survial after Cisplatin, Doxorubicin, Mitomycin-C, Ethiodol, and Polyvinyl Alcohol Chemoembolization", *Journal of Vascular and Interventional Radiology*, vol. 12, No. 2, pp. 187-193, Feb. 2001.

Ramos, et al., "Tumor vascular signals in renal masses: detection with Doppler US", *Radiology*, vol. 168, No. 3, pp. 633-637, 1988.

Ravina, J.H. et al., "Advantage of Pre-Operative Embolization of Fibroids: About a Multicentric Set of 31 Cases", *Contracept. Fertil. Sex.*, vol. 23, No. 1, pp. 45-49, Jan. 1995 (abstract).

Ravina, J.H. et al., "Arterial Embolisation to Treat Uterine Myomata", *Lancet*, vol. 346, pp. 671-674, Sep. 9, 1995.

Ravina, J.H. et al., "Interest of Particulate Arterial Embolization in the Treatment of Some Uterine Myoma", *Bull. Acad. Natle. Med.*, vol. 181, No. 2, pp. 233-246, Feb. 4, 1997 (Summary).

Repa, I. et al., "Mortalities Associated with Use of a Commercial Suspension of Polyvinyl Alcohol," *Radiology*, 170(2):395-399 (Feb. 1989).

Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).

Rump, A. et al., "Pharmacokinetics of Intraarterial Mitomycin C in the Chemoembolisation Treatment of Liver Metastases," *Gen. Pharmac.*, 27(4):669-671 (1996).

Schetky, "Shape-Memory Alloys," *Encyclopedia of Chemical Technology*, Third Edition, vol. 20, John Wiley & Sons, New York, pp. 726-736 (1982).

Schlief, R. et al., "Enhanced Color Doppler Echocardiography of the Left Heart After Intravenous Injection of a New Saccharide Based Agent in Humans", *Circulation*, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", *Echocardiography*, vol. 7, No. 1, pp. 61-64, Jan. 1990.

Schwarz et al., "The acoustic filter: An ultrasonic blood filter for the heart-lung machine," *J. Thorac. Cardiovasc. Surg.*, 104(6):1647-1653 (Dec. 1992).

Shafik, "Intraesophageal Polytef injection for the treatment of reflux esophagitis," *Surg. Endosc.*, 10:329-331 (1996).

Shape Shifters, http://www.sciam.com/tehbiz/0501scicit6.html, 3 pages, 2001.

Shung, K.K. et al., "Scattering of Ultrasound by Blood", *IEEE Transactions on Biomedical Engineering*, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", *Journal of Acoustical Society of America*, vol. 53, No. 4, pp. 1351-1355, Apr. 1973.

SIR-Spheres (Yttrium-90 Microspheres), pp. 1-12.

SIR-Spheres, Radioactive Implant (Yttrium-90 Microspheres), Sirex Medical, Inc., San Diego, CA, Nov. 6, 2000, pp. 1-15.

Sirtex Medical Limited—Product Description http://www.sirtex.com/?p=72, 3 pages (Retrieved from the internet on May 27, 2003).

Sirtex Medical Limited—Targeted Radiotherapy with SIR-Spheres http://www.sirtex.com/?p=57, 2 pages (Retrieved from the internet on May 27, 2003).

Siskin et al., "Pathologic Evaluation of a Spherical Polyvinyl Alcohol Embolic Agent in a Porcine Renal Model," *J. Vasc. Interv. Radiol.*, 14:89-98 (2003).

Skotland, T. et al., "In Vitro Stability Analyses as a Model for Metabolism of Ferromagnetic Particles (Clariscan™), a Contrast Agent for Magnetic Resonance Imaging", *J. Pharm. Biomed. Anal.*, vol. 28, No. 2, pp. 323-329, Apr. 15, 2002.

"Smart Sutures Tie Themselves", Apr. 26, 2002, http://www.sciam.com/article.cfm?articleID=00047706-121F-1CD0-B4A8809EC588, 2 pages.

Smith et al., "Evaluation of Polydimethylsiloxane as an alternative in the Endoscopic Treatment of Vesicoureteral Reflux," *The Journal of Urology*, 152:1221-1224 (Oct. 1994).

Smith et al., "Left Heart Opacification with Peripheral Venous Injection of a New Saccharide Echo Contrast Agent in Dogs", *JACC*, vol. 13, No. 7, pp. 1622-1628, Jun. 1989.

Soppimath et al., "Controlled release of antihypertensive drug from the interpenetrating network poly(vinyl alcohol)-guar gum hydrogel microspheres," *J. Biomater. Sci. Polymer Edn*, 11(1):27-43 (2000).

Spickler, et al., "The MR appearance of endovascular embolic agents in vitro with clinical correlation", *Comput Med Imaging Graph*, vol. 14, No. 6, pp. 415-423, 1990.

Spies JB, "Georgetown University Medical Center. Uterine Fibroid Embolization (UFE). An alternative to surgery for patients with uterine fibroids. Literature Review," http://www.fibroidoptions.com/pr-lit.htm, 6 pages, Sep. 1, 2001.

Stancato-Pasik, A. et al., "Obstetric Embolotherapy: Effect on Menses and Pregnancy", *Radiology*, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", *Clinical Cancer Research*, vol. 5, No. 10, pp. 3079-3087, Oct. 1999 (Supplement).

Strasnick et al., "Transcutaneous Teflon® Injection for Unilateral Vocal Cord Paralysis: An Update," *The Laryngoscope*, 101:785-787 (Jul. 1991).

Stridbeck, H. et al, "Collateral Circulation Following Repeated Distal Embolization of the Hepatic Artery in Pigs," *Invest. Radiol.*, 19(3):179-183 (1984).

Strunk, et al., "Treatment of congenital coronary arteriovenous malformations with microparticle embolization", *Cathet Cardiovasc Diagn*, vol. 22, No. 2, pp. 133-136, 1991.

Swanson DA et al., "The role of embolization and nephrectomy in the treatment of metastatic renal carcinoma", *Urologic Clinics of North America*, 7(3):719-730, 1980. University of Pennsylvania Cancer Center—Oncolink, http://www.oncolink.upenn.edu/pdg_html/cites/00/00585.html.

Tabata et al., "Tumor accumulation of poly(vinyl alcohol) of different sizes after intravenous injection", *Journal of Controlled Release*, vol. 50, pp. 123-133, Jan. 2, 1998.

Tadavarthy et al., "Polyvinyl Alcohol (Ivalon)—A New Embolic Material", *The American Journal of Roentgenology Radium Therapy and Nuclear Medicine*, vol. 125, No. 3, pp. 609-616, Nov. 1975.

Tadavarthy et al., "Polyvinyl Alcohol (Ivalon) as an Embolizing Agent", *Seminars in Interventional Radiology*, vol. 1, No. 2, pp. 101-109, Jun. 1984.

Tamatani, S. et al., "Histological Interaction of Cultured Endothelial Cells and Endovascular Embolic Materials Coated with Extracellular Matrix", *J. Neurosurg.*, vol. 86, No. 1, pp. 109-112, Jan. 1997.

Tao, et al., "Study of microspheres for embolization of hepatic artery", *Acta Pharmaceutica Sinica*, vol. 23, No. 1, pp. 55-60, 1988.

Tao, et al., "Study of microspheres for embolization of hepatic artery", (Translation) *Acta Pharmaceutica Sinica*, vol. 23, No. 1, pp. 55-60, 1988.

Terada, et al., "Preoperative embolization of meningiomas fed by ophthalmic branch arteries", *Surg Neurol*, vol. 45, No. 2, pp. 161-166, 1996.

Thanoo, et al., "Controlled release of oral drugs from cross-linked polyvinyl alcohol microspheres", *J Pharm Pharmacol*, vol. 45, No. 1, pp. 16-20, 1993.

Thanoo, B. C. et al., "Preparation and Properties of Barium Sulphate and Methyl Iothalamate Loaded Poly(vinyl Alcohol) Microspheres as Radiopaque Particulate Emboli," *Journal of Applied Biomaterials*, 2:67-72 (1991).

Thanoo, et al., "Tantalum loaded silicone micropsheres as particulate emboli", *J Microencapsul*, vol. 8, No. 1, pp. 95-101, 1991.

Thelen, V.M. et al., "Catheter Embolisation of Metastasising Renal Carcinomas Using Butyle-2-cyano-acrylate", *Fortschr. Rontgenstr.*, vol. 124, No. 3, pp. 232-235, Mar. 1976 (Abstract).

The Fibroid Embolization Center of the New York United Hospital Medical Center, "Fibroid Facts," http://www.uhmc.com/fibro2.htm, 9 pages.

The Vanderbilt-Ingram Cancer Center, "Kidney Cancer," http://www.mc.Vanderbilt.Edu/cancer/cancerinfo/kidney.html, 1 page, 2001.

Tian et al., "Design and synthesis of amphiphilic poly (ethylene glycol) derivatives as micellar drug delivery systems," *Polymer Preprints*, 43(2):719-720 (Fall 2002).

Tikkakoski, et al., "Preoperative embolization in the management of neck paragangliomas", *Laryngoscope*, vol. 107, pp. 821-826, 1997.

Toon, "Improving a Key Weapon Against Cancer," Research Horizons, pp. 11-12, Spring/Summer 2001.

Touho, et al., "Intravascular treatment of spinal arteriovenous malformations using a microcatheter—with special reference to serial xylocaine tests and intravascular pressure monitoring", *Surgical Neurology*, vol. 42, No. 2, pp. 148-156, 1994.

UCLA Radiological Sciences, "A summary of terms appearing in this text," http://www.radsci.ucla.edu:8000/aneurysm/terms.html, 1 page.

University Medical Center SUNY Stony Brook, Department of Urology, "Variococele and its treatment," http://www.hsc.sunysb.edu/urology/male_inf...variocoele_and_its_treatment.html, 8 pages, Last Updated on Mar. 12, 2001.

Vivas S et al., "Arterioportal fistula and hemobilia in a patient with hepatic transplant", Gastroenterol Hepatol, 21(2):88-9, http://www.doyma.es/copiani/revistas/gastro/abstr/abs_p080.html, Feb. 1998 (Abstract).

Vogel F, "Nonsurgical Management of Uterine Fibroids," http://www.holyname.org/brochure/fibroids.html, 5 pages.

Wakhloo, et al., "Extended preoperative polyvinyl alcohol microembolization of intracranial meningiomas: Assessment of two embolization techniques", *American Journal of Neuroradiology*, vol. 14, pp. 571-582, 1993.

Walker WJ, "Non Surgical Treatment of Fibroids in the UK by Uterine Artery Embolisation—An Alternative to Hysterectomy, Myomectomy and Myolysis," http://www.fibroids.co.uk/thepaper.html, 2 pages, 2002.

Walsh RM et al., "Role of Angiography and Embolization for Acute Massive Upper Gastronintestinal Hemorrhage," *J. Gastrointest. Surg.*, 3:61-66 (1999).

Waltman, A.C. et al., "Technique for Left Gastric Artery Catheterization", *Radiology*, vol. 109, No. 3, pp. 732-734, Dec. 1973.

White, Jr., "Embolotherapy in Vascular Disease," *American Journal of Roentgenology*, 142:27-30 (Jan. 1984).

Widder, K.J. et al., "Selective Targeting of Magnetic Microspheres Containing Adriamycin: Total Remission in Yoshida Sarcoma-Bearing Rats", *Proceedings of the 16th Annual Meeting of American Society of Clinical Oncology*, May 26-27, 1980, San Diego, CA, p. 261.

Widder, K. et al., "Magnetic Microspheres: Synthesis of a Novel Parenteral Drug Carrier", *Journal of Pharmaceutical Sciences*, vol. 68, No. 1, pp. 79-82, Jan. 1979.

Wikholm G et al., "Embolization of Cerebral Arteriovenous Malformations: Part I—Technique, Morphology, and Complications", *Neurosurgery*, 39(3):448-459 (Sep. 1996).

Winters et al., "Periurethral injection of collagen in the treatment of intrinsic sphincteric deficiency in the female patient," *The Urologic Clinics of North America*, 22(3):673-678 (Aug. 1995).

Worthington-Kirsch RL, "Interventionalists offer management option for uterine fibroids," *Diagnostic Imaging*, 21(3):47-49, Mar. 1999, http://www.dimag.com/references/9903wortrefs.html.

Worthington-Kirsch, et al., "Uterine arterial embolization for the management of leiomyomas: Quality-of-life assessment and clinical response", *Radiology*, vol. 208, No. 3, 625-629, 1998.

Wright, K.C. et al., "Partial Splenic Embolization Using Polyvinyl Alcohol Foam, Dextran, Polystyrene, or Silicone," *Radiology*, 142:351-354, Feb. 1982.

Wu, A.M., "Engineered Antibodies for Breast Cancer Imaging and Therapy," http://www.cbcrp.org/research/PageGrant.asp?grant_id=111, 3 pages, 1996.

Yamada, T. et al., "Extended Intraarterial Cisplatin Infusion for Treatment of Gynecologic Cancer After Altercation of Intrapelvic Blood Flow and Implantation of a Vascular Access Device", *Cardiovasc. Intervent. Radiol.*, vol. 19, pp. 139-145, 1996.

Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.

Yoon et al., "Surface Immobilization of Galactose onto Aliphatic Biodegradable Polymers for Hepatocyte Culture," *Biotechnol. Bioeng.*, 78(1):1-10 (Apr. 5, 2002).

Yusi et al., "Submuscosal Injection of Polyvinyl Alcohol in Artificially Created Vesico-Ureteral Reflux: A Preliminary Report," *Asian J. Surg.*, 18(2):122-127 (Apr. 1995).

Zisch et al., "Covalently conjugated VEGF-fibrin matrices for endothelialization," *Journal of Controlled Release*, 72:101-113 (2001).

Ziskin, M.C. et al., "Contrast Agents for Diagnostic Ultrasound", *Investigative Radiology*, vol. 7, No. 6, pp. 500-505, Nov.-Dec. 1972.

Zou, Ying-hua, et al. "Experimental Canine Hapatic Artery Embolization with Polyvinyl Alcohol Microspheres," *Zhong Hua Fang-She Xue ZaZhi*, 23(6):330-332 (1989).

Zou, Ying-hua, et al. "Experimental Canine Hapatic Artery Embolization with Polyvinyl Alcohol Microspheres," Translation, *Zhong Hua Fang-She Xue ZaZhi*, 23(6):330-332 (1989).

U.S. Appl. No. 11/274,538 ("Medical Articles Having Enhanced Therapeutic Agent Binding", Tenney et al.), filed Nov. 15, 2005.

* cited by examiner

TISSUE-TREATMENT METHODS

TECHNICAL FIELD

This invention relates to tissue-treatment methods.

BACKGROUND

Energy, such as RF energy, can be employed to degrade unhealthy or unwanted tissue, such as a wart, a mole, a cyst, scar tissue, and/or a tumor. In some cases, for example, an RF probe can be delivered into the unhealthy or unwanted tissue via a catheter. Once positioned within the tumor, RF-emitting tines can be deployed and activated. Upon activation, the tines can emit RF energy to degrade the tissue by, for example, heating the tissue.

SUMMARY

The invention relates to polymer insulators and methods of using the same.

In one aspect, the invention features a method that includes separating a first portion of tissue of a subject from a second portion of tissue of the subject so that there is a space between the first and second portions of tissue. The method also includes disposing a material between the first and second portions of tissue, and exposing the first portion of tissue to energy to treat the first portion of tissue. The material disposed between the first and second portions of tissue can be one or more of the following: deionized water; a buffered saline solution; liquid polymers; gels; particles; foams; and/or gases.

In another aspect, the invention features a method that includes disposing a material between a first portion of tissue of a subject and a second portion of tissue of the subject. The method also includes exposing the first portion of tissue to energy to treat the first portion of tissue. The second portion of tissue can be substantially unexposed to the energy while the first portion of tissue is exposed to the energy. The distance between the first and second portions of tissue is at most about five centimeters, and the material disposed between the first and second portions of tissue can be one or more of the following: deionized water; a buffered saline solution; liquid polymers; gels; particles; foams; and/or gases.

The methods can include one or more of the following features.

In some embodiments, the second portion of tissue is substantially unexposed to the energy while the first portion of tissue is exposed to the energy.

In certain embodiments, the energy includes RF energy, microwave energy, ultrasonic energy, laser energy, and/or heat. In some embodiments, exposing the first portion of tissue to energy includes cooling the first portion of tissue.

In some embodiments, the first portion of tissue includes unhealthy tissue (e.g., cancerous tissue), and/or the second portion of tissue includes healthy tissue. Examples of tissue include bodily vessel tissue, bladder tissue, bone tissue, brain tissue, breast tissue, bronchi tissue, diaphragm tissue, esophagus tissue, gall bladder tissue, heart tissue, intestine tissue, kidney tissue, larynx tissue, liver tissue, lung tissue, lymph vessel tissue, lymph node tissue, nerve tissue, ovary tissue, pancreas tissue, prostate tissue, skin tissue, stomach tissue, and thyroid tissue, trachea tissue, urethra tissue, ureter tissue, uterus tissue, and vertebral disc tissue.

In certain embodiments, the material is formed of particles. The particles can have, for example, a size of at most about 10,000 microns. The particles can include one or more polymeric materials. The particles can include a material having a dielectric constant of at least about 2.1 and/or a dielectric strength of at least about 100 Kv/mm in some embodiments.

In some embodiments, the material is a liquid polymer.

In certain embodiments, the material is a foam.

In some embodiments, the material is a gas. Examples of gases include air, helium, neon, argon, krypton, xenon, nitrogen, and carbon dioxide.

In some embodiments, the material is deionized water and/or a buffered saline solution.

In certain embodiments, the material is a water soluble polysaccharide and/or an ionically cross-linkable polymer.

In certain embodiments, the material is a ceramic material.

In some embodiments, the material is capable of undergoing an endothermic reaction.

In some embodiments, the space between the first and second portions of tissue is at most about five centimeters.

The methods can provide one or more of the following advantages.

In some embodiments, the methods can protect healthy or desired tissue from damage, while treating (e.g., ablating, degrading, destroying) unhealthy or undesired tissue.

In certain embodiments, the methods can allow relatively small regions of desired or healthy tissue to be protected while treating (e.g., ablating, degrading, destroying) undesired or unhealthy tissue.

In certain embodiments, the methods can protect regions of desired or healthy tissue that are difficult to access.

Features and advantages are in the description, drawings, and claims.

DESCRIPTION OF DRAWINGS

Like reference symbols in the drawings indicate like elements.

DETAILED DESCRIPTION

The methods include disposing one or more materials between a region of unhealthy tissue and a region of healthy tissue, and exposing the unhealthy tissue to energy (e.g., RF energy) to damage or destroy the unhealthy tissue. The materials can include one or more of the following: deionized water; a buffered saline solution; liquid polymers; gels; particles; foams; and/or gases. The material disposed between the unhealthy and healthy tissue regions can protect the healthy tissue so that it is substantially unharmed by the energy.

Figure 1A:
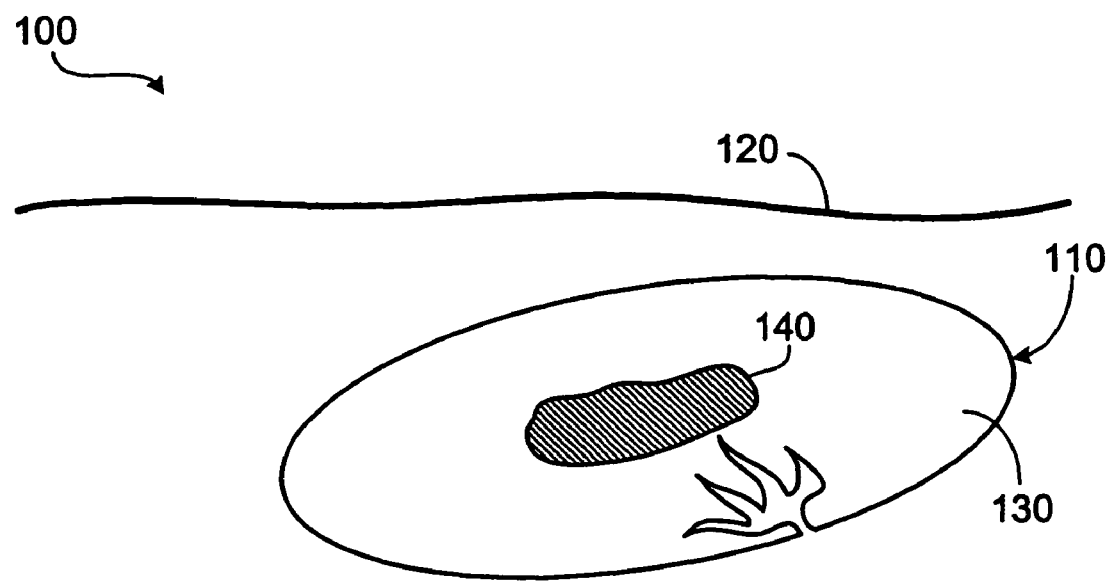
FIG. 1A is a cross-sectional view of a cancerous liver of a subject.

For example, FIG. 1A shows a portion 100 of a subject including a liver 110 and skin 120. Liver 110 includes healthy tissue 130 and unhealthy tissue 140 (e.g., a cancerous tissue, such as a cancerous tumor).

Figure 1B:
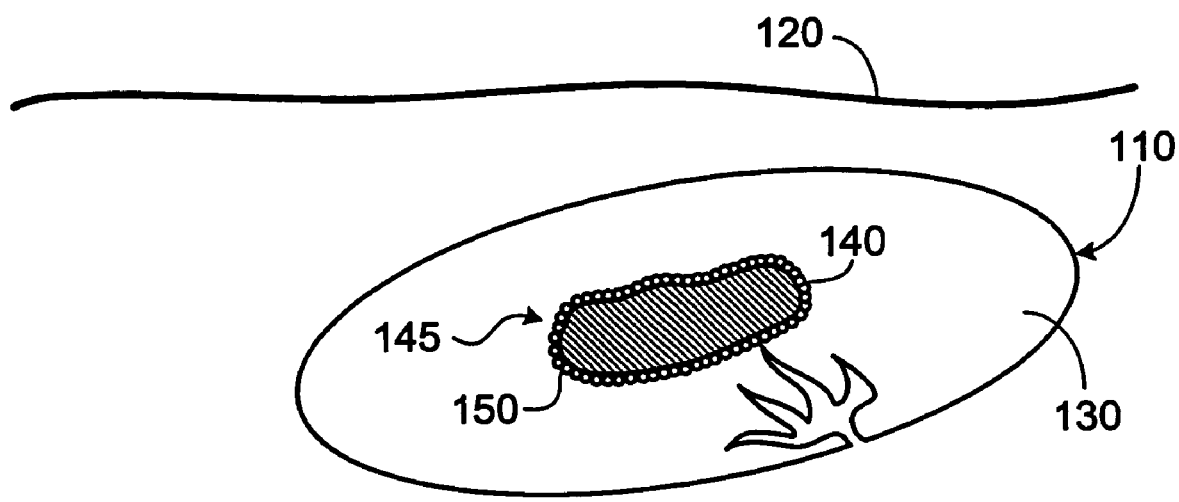
FIG. 1B is a cross-sectional view of the liver of FIG. 1A with a protective layer of particles disposed between the cancerous and non-cancerous tissue regions.

FIG. 1B shows healthy tissue 130 separated from unhealthy tissue 140 by a protective layer 145 of particles 150. As discussed in more detail below, particles 150 can protect healthy tissue 130 while unhealthy tissue 140 is treated with energy.

For example, particles 150 can be formed of a material that is a poor conductor of certain types of energy (e.g., RF energy) relative to tissues 130 and 140 of the subject. Thus, when inserted between healthy and unhealthy tissues 130, 140, particles 150 substantially prevent energy applied to unhealthy tissue 140 from harming healthy tissue 130. As a result, healthy tissue 130 is substantially protected from harm when energy is applied to unhealthy tissue 140.

In some embodiments, particles 150 are at least partially formed from one or more polymers. Examples of polymers include polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly (lactic-co-glycolic) acids (e.g., poly(d-lactic-co-glycolic) acids), polypropylene, polytetrafluorethylene, polyethyleneterephthalate, polycarbonate, polyphenyleneoxide, polysulfone, polyhydantoine, polyamide-imide, polyimide, cellulose triacetate, cellulose acetate butyrate, and copolymers or mixtures thereof.

Additional examples of materials from which particles 150 can be at least partially formed include alginates (e.g., sodium alginate), alginate salts, xanthan gums, natural gum, agar, agarose, chitosan, carrageenan, fucoidan, furcellaran, laminaran, hypnea, eucheuma, gum arabic, gum ghatti, gum karaya, gum tragacanth, hyalauronic acid, locust beam gum, arabinogalactan, pectin, amylopectin, other water soluble polysaccharides and other ionically cross-linkable polymers.

In some embodiments, particles 150 are at least partially formed of a bio-absorbable and/or bio-erodible material, such as a polysaccharide (such as an alginate); a polysaccharide derivative; a water soluble polymer (such as a polyvinyl alcohol, e.g., that has not been cross-linked); biodegradable poly DL-lactide-poly ethylene glycol (PELA); a hydrogel (e.g., polyacrylic acid, haluronic acid, gelatin, carboxymethyl cellulose); a polyethylene glycol (PEG); chitosan; a polyester (e.g., a polycaprolactone); a poly(lactic-acid) (PLA); a poly (lactic-co-glycolic) acid (e.g., a poly(d-lactic-co-glycolic) acid); or a combination thereof.

In certain embodiments, particles 150 are at least partially formed of one or more ceramic materials. In general, a ceramic material contains one or more metallic elements and one or more non-metallic elements. Examples of ceramics include metal oxides, such as aluminum oxide, cerium oxide, copper oxide, iron oxide, magnesium oxide, and potassium oxide.

In some embodiments, particles 150 can be formed of a glass. Examples of glasses include oxides of silicon, beryllium, boron, germanium, phosphorous, vanadium, lead, tin, zinc, zirconium, and titanium, as well as such nonoxide compounds as germanium sulphide, metal fluorides, and iodites. Other examples of glasses include certain metallic selenides, tellurides, arsenides, phosphides, and obsidian.

In certain embodiments, particles 150 contain encapsulated air (e.g., to enhance the protective ability of particles 150). In some embodiments, particles 150 contain an encapsulated composition capable of undergoing an endothermic reaction. For example, particles 150 can encapsulate a ammonium nitrate and water composition. Consequently, particles 150 can absorb greater amounts of energy (e.g., heat) in some cases.

In some embodiments, particles 150 are formed from a material that has a relatively high dielectric constant. For example, particles 150 can have a dielectric constant that is higher than the dielectric constant of tissues 130 and 140. This can, for example, allow protective layer 145 to be a relatively poor conductor of RF energy. For example, particles 150 can be formed of a material having a dielectric constant of at least about 2.0 (e.g., at least about 2.1, at least about 2.7, at least about 3.1). In some embodiments, particles 150 can be formed of a material having a dielectric constant of from about 2.0 to about 4.5 (e.g., from about 2.1 to about 4.5, from about 2.7 to about 4.5, from about 3.1 to about 4.5). The term dielectric constant, as used herein, is measured by ASTM D150 at 50 Hz and 20° C.

In some embodiments, the material from which particles 150 are made has a relatively high dielectric strength. For example, particles 150 can have a dielectric strength that is higher than the dielectric strength of tissues 130 and 140. This can, for example, allow layer 145 to be a relatively poor conductor of RF energy. For example, particles 150 can be formed of a material having a dielectric strength of at least about 100 kV/mm (e.g., at least about 200 kV/mm, at least about 240 kV/mm, at least about 280 kV/mm). In some embodiments, particles 150 can be formed of a material having a dielectric strength of from about 50 kV/mm to about 350 kV/mm (e.g., from about 100 kV/mm to about 300 kV/mm, from about 200 kV/mm to about 300 kV/mm, from about 240 kV/mm to about 300 kV/mm, from about 280 kV/mm to about 300 kV/mm). The term dielectric strength, as used herein, is measured by ASTM D149.

In certain embodiments, particles 150 can be formed of a material having a relatively high dissipation factor. For example, particles 150 can have a dissipation factor that is higher than the dissipation factor of tissues 130 and 140. This can, for example, allow layer 145 to be a relatively poor conductor of RF energy. For example, particles 150 can be formed of a material having a dissipation factor of at least about 0.2 (e.g., at least about 0.7, at least about 1.5, at least about nine, at least about 21). The term dissipation factor, as used herein, is measured by ASTM D150 at 50 Hz and 20° C.

In some embodiments, particles 150 can be formed of a material having a relatively high volume resistivity. For example, particles 150 can have a volume resistivity that is higher than the volume resistivity of tissues 130 and 140. This can, for example, allow layer 145 to be a relatively poor conductor of RF energy. For example, particles 150 can be formed of a material having a volume resistivity of at least about $10^6$ to about $10^{17}$ ohm-cm (e.g., at least about $10^{14}$ ohm-cm, at least about $10^{16}$ ohm-cm, at least about $10^{17}$ ohm-cm). As used herein, the volume resistivity of a particle is measured by ASTM D257-99.

In certain embodiments, particles 150 can be formed of a material having a relatively low surface resistivity. For example, particles 150 can have a surface resistivity that is lower than the surface resisitivity of tissues 130 and 140. For example, particles 150 can be formed of a material having a surface resistivity of at most about $10^{12}$ to about $10^{16}$ ohm-cm (e.g., at most about $10^{16}$ ohm-cm, at most about $10^{14}$ ohm-cm, at most about $10^{12}$ ohm-cm). The term surface resistivity, as used herein, is measured by ASTM D257-99.

In certain embodiments, the material from which particles 150 are made can be chosen based on the intensity and/or type of energy used to treat unhealthy tissue 140. As an example, in embodiments in which RF energy and/or microwave energy is used, it can be beneficial to use particles formed of a material with a higher dielectric constant and/or a higher dielectric strength. As an additional example, in embodiments in which ultrasonic energy is used, it can be beneficial to use particles formed of a material that can retard the transmission of ultrasonic energy therethrough. As another example, in embodiments in which laser energy is used, it can be beneficial to use particles formed of a material that is capable of absorbing and/or refracting laser energy.

In some embodiments, particles 150 have a diameter of no greater than about 10,000 microns (e.g., no greater than about 7,500 microns, no greater than about 5,000 microns, no greater than about 2,500 microns, no greater than about 2,000 microns, no greater than about 1,5000 microns, no greater than about 1,000 microns, no greater than about 500 microns, no greater than about 400 microns, no greater than about 300 microns, no greater than about 200 microns, no greater than about 100 microns). In some embodiments, particles 150 have a diameter of about 100 microns to about 10,000 microns (e.g., about 100 microns to about 1000 microns, about 100 microns to 500 microns, about 2,500 microns to about 5,000 microns, about 5,000 microns to about 10,000 microns, about 7,500 microns to about 10,000 microns).

Figure 1C:
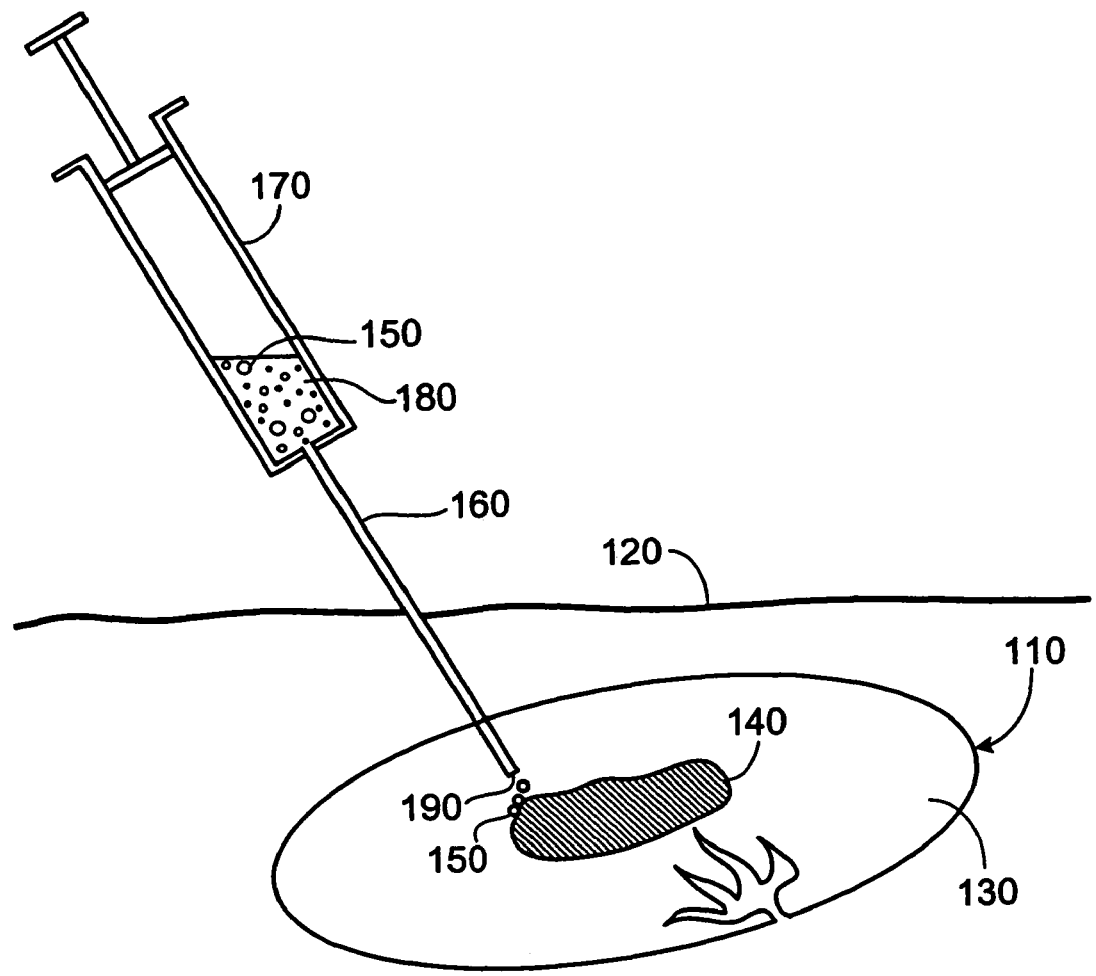
FIG. 1C illustrates administration of particles between cancerous and non-cancerous tissue regions of the liver of FIG. 1A.

FIG. 1C shows a method of disposing particles 150 between healthy tissue 130 and unhealthy tissue 140 using a needle 160. Needle 160 is in fluid communication with a syringe 170, which contains particles 150 suspended in a carrier fluid 180. An end 190 of needle 160 is inserted through skin 120 of the subject and into healthy tissue 130. Needle 160 is inserted until end 190 is positioned between healthy and unhealthy tissues 130, 140 in order to separate healthy tissue 130 from unhealthy tissue 140 and form a gap between healthy and unhealthy tissues 130, 140. Particles 150 and carrier fluid 180 are then injected from syringe 170 into the gap to form protective layer 145. In some embodiments, this process is repeated until protective layer 145 reaches a desired thickness. In certain embodiments, the method is performed so that protective layer 145 covers only a particular region or regions of unhealthy tissue 140. For example, any of various imaging modalities, such as ultrasound, CT, MRI, and/or fluoroscopy, can be used to help the user (e.g., a physician) to position needle 160 in a targeted region of the tissue. Consequently, particles 150 can be disposed (e.g., injected) substantially only in the targeted region. It may be unnecessary, for example, to completely separate healthy tissue 130 from unhealthy tissue 140 when only a particular region of healthy tissue 130 is exposed to energy emitted during a treatment. In such cases, particles 150 can be restricted to regions likely to be exposed to the energy.

Carrier fluid 180 can be a pharmaceutically acceptable carrier, such as a buffered saline solution, non-ionic contrast agent, therapeutic agent, or a combination of these carriers. In some embodiments, carrier fluid 180 includes deionized water, water for injection, liquid polymer, gel polymer, gas, or a combination of these carriers. Carrier fluid 180, in some cases, can contribute to the protection of healthy tissue 130. In certain embodiments, carrier fluid 180 includes one or more insulating materials, such as glass fibers. The insulating materials can enhance the ability of carrier fluid 180 to contribute to the protection of healthy tissue 130.

In some embodiments, particles 150 are not suspended in a carrier fluid. For example, particles 150 alone can be contained within syringe 170, and injected from syringe 170 into the gap between healthy tissue 130 and unhealthy tissue 140.

While embodiments have been described in which a needle is used to form the opening between healthy tissue 130 and unhealthy tissue 140, in some embodiments, other techniques can be used to form this opening. For example, the opening can be formed using an open procedure in which an incision is made in the subject to gain access to unhealthy tissue 140. As another example, blunt dissection techniques may be used to form the opening between healthy tissue 130 and unhealthy tissue 140. After forming the opening, healthy tissue 130 can be separated from unhealthy tissue 140 using any of various techniques. For example, a needle can be injected between healthy and unhealthy tissues 130, 140. As another example, one or more gases or liquids can be pumped into the region between healthy tissue 130 and unhealthy tissue 140. After separating healthy tissue 130 from unhealthy tissue 140, particles 150 can be implanted within a gap created between the separated healthy and unhealthy tissues 130, 140 using any of various techniques. For example, in some embodiments, particles 150 can be injected into the gap via a needle, directly from a syringe, or a catheter.

Figure 1D:
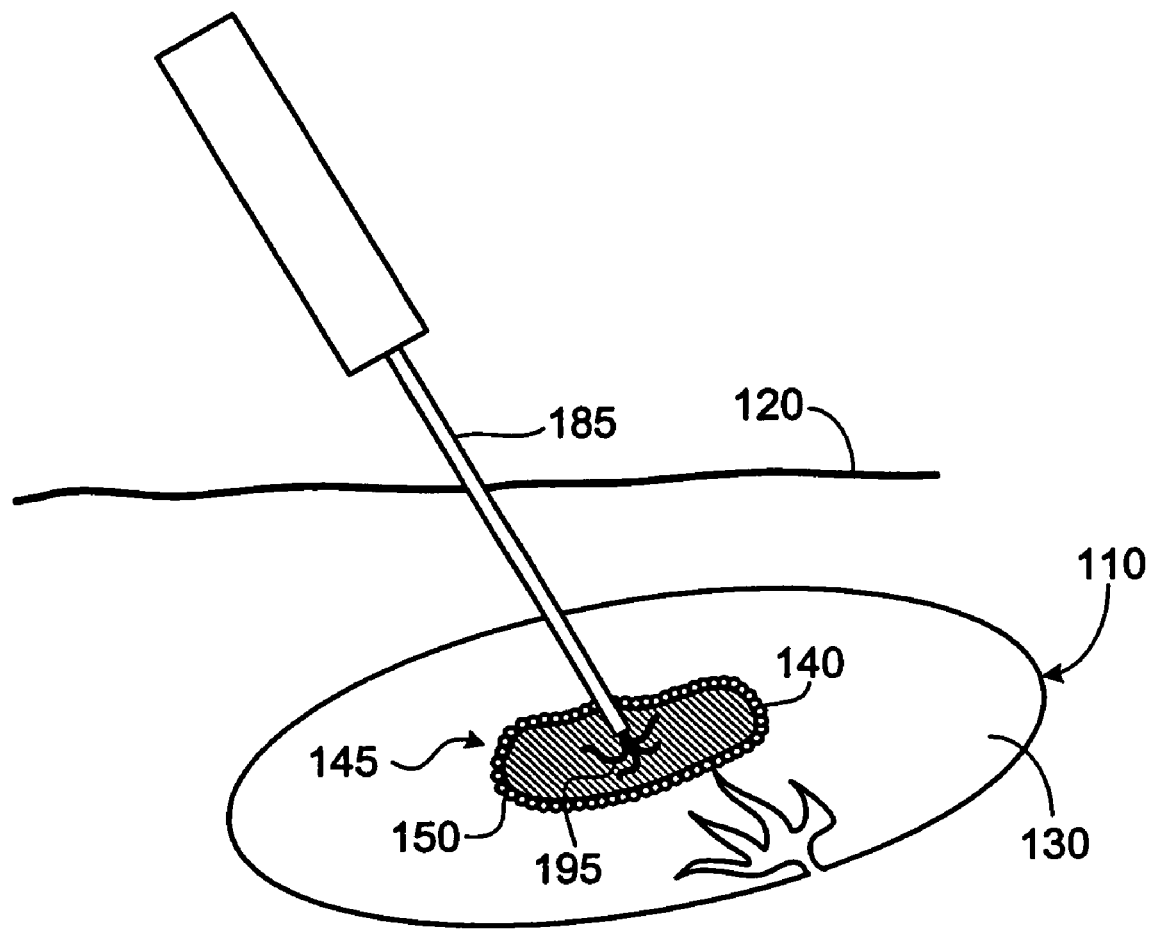
FIG. 1D illustrates emission of energy within the cancerous tissue region of the liver of FIGS. 1A, 1B, and 1C to degrade the cancerous tissue.

FIG. 1D illustrates a method of treating unhealthy tissue 140 with RF energy using an RF probe 185 (e.g., a 3.5 centimeter coaxial LeVeen electrode, available from Boston Scientific Corporation). Probe 185 is positioned within unhealthy tissue 140 (e.g., by insertion through skin 120 of the subject). Once positioned within unhealthy tissue 140, tines 195 of RF probe 185 are deployed within unhealthy tissue 140, and RF probe 185 is activated so that RF energy is emitted from tines 195. The RF energy emitted from tines 195 can heat unhealthy tissue 140 around tines 195 to treat (e.g., ablate, damage destroy) portions of unhealthy tissue 140 that are exposed to the energy.

Protective layer 145 substantially prevents the RF energy from penetrating healthy tissue 130 when unhealthy tissue 140 is exposed to the RF energy. For example, the RF energy is prevented from penetrating healthy tissue 130 with a substantially harmful intensity. Thus, the method can be used to treat unhealthy tissue 140 without substantially harming healthy tissue 130.

The level of protection provided by protective layer 145 of particles 150 can be a function of the thickness of protective layer 145. As an example, in some embodiments, as the thickness of protective layer 145 increases, its ability to conduct energy (e.g., heat and/or RF energy) can decrease, and, as the thickness of protective layer 145 decreases, its ability to conduct energy (e.g., heat and/or RF energy) can decrease. In such embodiments, it can become more difficult for energy to be transported from unhealthy tissue 140 to healthy tissue 130 via protective layer 145 as the thickness of protective layer 145 increases, and it can become easier for energy to be transported from unhealthy tissue 140 to healthy tissue 130 via protective layer 145 as the thickness of protective layer 145 decreases. Thus, it may be beneficial to increase the thickness of protective layer 145 as the intensity of the energy used to treat unhealthy tissue 140 increases, and to decrease the thickness of protective layer 145 as the intensity of energy decreases (e.g., to obtain a desired degree of insulation while keeping the space between unhealthy tissue 140 and healthy tissue 130 relatively small to decrease possible trauma to the subject).

The thickness of protective layer 145 can be modified using any of various techniques. For example, the thickness of protective layer 145 can be increased or decreased by increasing or decreasing the size of particles 150, and/or by disposing a greater or lesser number of particles across a thickness of the gap between healthy and unhealthy tissues 130, 140. In certain embodiments, multiple layers of particles 150 are disposed between healthy tissue 130 and unhealthy tissue 140 in order to increase the thickness of protective layer 145.

In some embodiments, after separating healthy tissue 130 from unhealthy tissue 140, the gap between healthy and unhealthy tissues 130, 140 can be at most about five centimeters (e.g., at most about four centimeters, at most about three centimeters, at most about two centimeters, at most about one centimeter, at most about 0.5 centimeter, at most about 0.25 centimeter, or at most about 0.1 centimeter). For example, protective layer 145 of particles 150 can have a thickness of at most about five centimeters (e.g., at most about four centimeters, at most about three centimeters, at most about two centimeters, at most about one centimeter, at most about 0.5 centimeter, at most about 0.25 centimeter, or at most about 0.1 centimeter). In some embodiments the gap between healthy and unhealthy tissues 130, 140 can be about 0.1 centimeter to about five centimeters (e.g., about 0.1 centimeter to about three centimeters, about 0.1 centimeter to about one centimeter, about 0.1 centimeter to about 0.5 centimeter, about 0.1 centimeter to about 0.25 centimeter). For example, protective layer 145 of particles 150 can have a thickness of about 0.1 centimeter to about five centimeters (e.g., about 0.1 centimeter to about three centimeters, about 0.1 centimeter to about one centimeter, about 0.1 centimeter to about 0.5 centimeter, about 0.1 centimeter to about 0.25 centimeter).

In certain embodiments, particles 150 include one or more therapeutic agents (e.g., drugs) that can be delivered to healthy and/or unhealthy tissues 130, 140. The therapeutic agent(s) can be in and/or on the particle. Therapeutic agents include agents that are negatively charged, positively charged, amphoteric, or neutral. Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; gene therapies; nucleic acids with and without carrier vectors; oligonucleotides; gene/vector systems; DNA chimeras; compacting agents (e.g., DNA compacting agents); viruses; polymers; hyaluronic acid; proteins (e.g., enzymes such as ribozymes); immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); calcium entry blockers; and survival genes which protect against cell death.

Exemplary non-genetic therapeutic agents include: anti-thrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, sulfasalazine and mesalamine; antineoplastic/anti-proliferative/anti-mitotic agents such as paclitaxel, 5-fluorouracil, cisplatin, doxorubicin; vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, anti-thrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Exemplary genetic therapeutic agents include: anti-sense DNA and RNA; DNA coding for: anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor a, hepatocyte growth factor and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Vectors of interest for delivery of genetic therapeutic agents include: Plasmids, Viral vectors such as adenovirus (AV), adenoassociated virus (AAV) and lentivirus, Non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents appropriate for the practice of the present invention are disclosed in U.S. Pat. No. 5,733,925, which is incorporated herein by reference. Therapeutic agents disclosed in this patent include the following: "Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

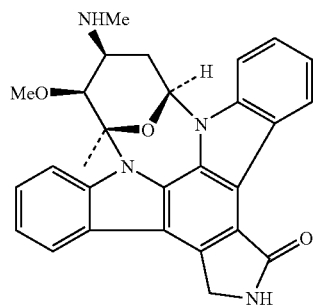

as well as diindoloalkaloids having one of the following general structures:

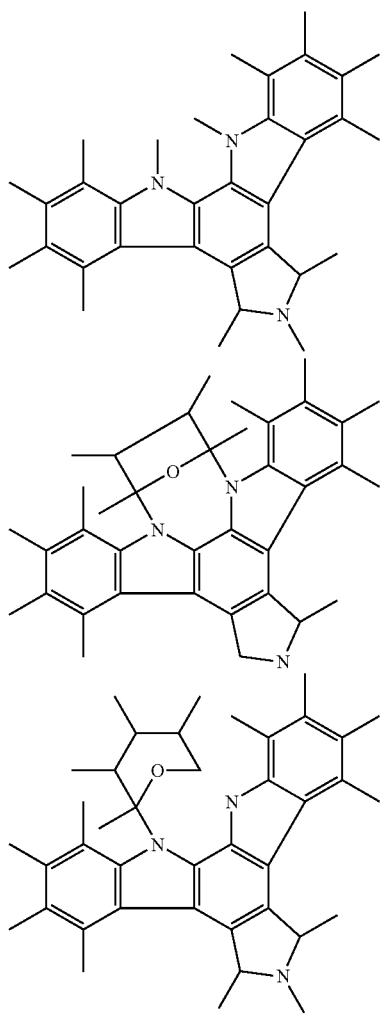

as well as stimulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like.

Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or I2.

Agents that inhibit the intracellular increase in cell volume (i.e., the tissue volume occupied by a cell) such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, Pseudomonas exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, Pseudomonas exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents are appropriate for the practice of the present invention and include one or more of the following:

Calcium-channel blockers including:
    Benzothiazapines such as diltiazem and clentiazem
    Dihydropyridines such as nifedipine, amlodipine and nicardapine
    Phenylalkylamines such as verapamil
Serotonin pathway modulators including:
    5-HT antagonists such as ketanserin and naftidrofuryl
    5-HT uptake inhibitors such as fluoxetine
Cyclic nucleotide pathway agents including:
    Phosphodiesterase inhibitors such as cilostazole and dipyridamole
    Adenylate/Guanylate cyclase stimulants such as forskolin
    Adenosine analogs
Catecholamine modulators including:
    α-antagonists such as prazosin and bunazosine
    β-antagonists such as propranolol
    α/β-antagonists such as labetalol and carvedilol
Endothelin receptor antagonists
Nitric oxide donors/releasing molecules including:
    Organic nitrates/nitrites such as nitroglycerin, isosorbide dinitrate and amyl nitrite
    Inorganic nitroso compounds such as sodium nitroprusside
    Sydnonimines such as molsidomine and linsidomine Nonoates such as diazenium diolates and NO adducts of alkanediamines S-nitroso compounds including low molecular weight compounds (e.g., S-nitroso derivatives of captopril, glutathione and N-acetyl penicillamine), high molecular weight compounds (e.g., S-nitroso derivatives of proteins, peptides, oligosaccharides, polysaccharides, synthetic polymers/oligomers and natural polymers/oligomers)

C-nitroso-, O-nitroso- and N-nitroso-compounds L-arginine

ACE inhibitors such as cilazapril, fosinopril and enalapril

ATII-receptor antagonists such as saralasin and losartin

Platelet adhesion inhibitors such as albumin and polyethylene oxide

Platelet aggregation inhibitors including:
    Aspirin and thienopyridine (ticlopidine, clopidogrel)
    GP IIb/IIIa inhibitors such as abciximab, epitifibatide and tirofiban Coagulation pathway modulators including:
    Heparinoids such as heparin, low molecular weight heparin, dextran sulfate and β-cyclodextrin tetradecasulfate
    Thrombin inhibitors such as hirudin, hirulog, PPACK (D-phe-L-propyl-L-arg-chloromethylketone) and argatroban
    FXa inhibitors such as antistatin and TAP (tick anticoagulant peptide)
    Vitamin K inhibitors such as warfarin
    Activated protein C Cyclooxygenase pathway inhibitors such as aspirin, ibuprofen, flurbiprofen, indomethacin and sulfinpyrazone Natural and synthetic corticosteroids such as dexamethasone, prednisolone, methprednisolone and hydrocortisone Lipoxygenase pathway inhibitors such as nordihydroguairetic acid and caffeic acid Leukotriene receptor antagonists Antagonists of E- and P-selectins Inhibitors of VCAM-1 and ICAM-1 interactions Prostaglandins and analogs thereof including:
    Prostaglandins such as PGE1 and PGI2
    Prostacyclin analogs such as ciprostene, epoprostenol, carbacyclin, iloprost and beraprost Macrophage activation preventers including bisphosphonates HMG-CoA reductase inhibitors such as lovastatin, pravastatin, fluvastatin, simvastatin and cerivastatin Fish oils and omega-3-fatty acids Free-radical scavengers/antioxidants such as probucol, vitamins C and E, ebselen, trans-retinoic acid and SOD mimics Agents affecting various growth factors including:
    FGF pathway agents such as bFGF antibodies and chimeric fusion proteins
    PDGF receptor antagonists such as trapidil
    IGF pathway agents including somatostatin analogs such as angiopeptin and ocreotide
    TGF-β pathway agents such as polyanionic agents (heparin, fucoidin), decorin, and TGF-β antibodies
    EGF pathway agents such as EGF antibodies, receptor antagonists and chimeric fusion proteins
    TNF-α pathway agents such as thalidomide and analogs thereof.

Thromboxane A2 (TXA2) pathway modulators such as sulotroban, vapiprost, dazoxiben and ridogrel Protein tyrosine kinase inhibitors such as tyrphostin, genistein and quinoxaline derivatives MMP pathway inhibitors such as marimastat, ilomastat and metastat Cell motility inhibitors such as cytochalasin B Antiproliferative/antineoplastic agents including:
    Antimetabolites such as purine analogs (6-mercaptopurine), pyrimidine analogs (e.g., cytarabine and 5-fluorouracil) and methotrexate
    Nitrogen mustards, alkyl sulfonates, ethylenimines, antibiotics (e.g., daunorubicin, doxorubicin), nitrosoureas and cisplatin
    Agents affecting microtubule dynamics (e.g., vinblastine, vincristine, colchicine, paclitaxel and epothilone)
    Caspase activators
    Proteasome inhibitors
    Angiogenesis inhibitors (e.g., endostatin, angiostatin and squalamine)
    Rapamycin, cerivastatin, flavopiridol and suramin Matrix deposition/organization pathway inhibitors such as halofuginone or other quinazolinone derivatives and tranilast Endothelialization facilitators such as VEGF and RGD peptide Blood rheology modulators such as pentoxifylline.

In some embodiments, particle 100 can include a combination of any of the above therapeutic agents.

Therapeutic agents are described, for example, in co-pending Published Patent Application No. US 2004/0076582 A1, published on Apr. 22, 2004, and entitled "Agent Delivery Particle", which is incorporated herein by reference, and in Pinchuk et al., U.S. Pat. No. 6,545,097, which is incorporated herein by reference.

Particles 150 can be formed using any of various systems and techniques, such as emulsion polymerization and/or droplet polymerization techniques. Examples of such systems and techniques are described, for example, in co-pending Published Patent Application No. US 2003/0185896 A1, published Oct. 2, 2003, and entitled "Embolization," and in co-pending Published Patent Application No. US 2004/0096662 A1, published May 20, 2004, and entitled "Embolization," each of which is incorporated herein by reference.

While certain embodiments have been described, other embodiments are also possible.

As an example, particles 150 can include (e.g., encapsulate) diagnostic agent(s) such as a radiopaque material, an MRI-visible material, a ferromagnetic material, and/or an ultrasound contrast agent. For example, particle 150 can encapsulate a ferromagnetic material so that the position of the particle in a lumen can be manipulated with a magnetic field. The magnetic field can be created outside the subject or inside the subject (e.g., via a magnetic catheter). Particles containing diagnostic agents are described in U.S. patent application Ser. No. 10/651,475, filed on Aug. 29, 2003, and entitled "Embolization", and magnetic devices are described in U.S. patent application Ser. No. 10/108,874, filed on Mar. 29, 2002, and entitled "Magnetically Enhanced Injection Catheter," both of which are incorporated herein by reference.

As an additional example, while embodiments have been described in which protective layer 145 is formed of particles, in some embodiments, protective layer 145 is formed of one or more liquid polymers. Examples of polymers from which a liquid polymer can be formed include those noted above. In some embodiments, a liquid polymer can be a carrier fluid for particles. A liquid polymer can be disposed between two portions of tissue using the methods described above (e.g., via a needle, a syringe, or a catheter).

As another example, in some embodiments, protective layer 145 is formed of one or more gels. A gel can be formed of, for example, one or more polymers. Examples of polymers include those noted above. A gel can be disposed between two portions of tissue using the methods described above (e.g., via a needle, a syringe, or a catheter).

As a further example, in some embodiments, protective layer 145 is formed from one or more gases. Examples of gases include helium, neon, argon, krypton, xenon, air, nitrogen, and carbon dioxide. In some embodiments, a gas can be a carrier fluid for particles. A gas can be disposed between two portions of tissue using the methods described above (e.g., via a needle, a syringe, or a catheter).

As an additional example, in some embodiments, protective layer 145 is formed from one or more foams. A foam can be formed of, for example, one or more polymers. Examples of polymers include those noted above. A foam can be disposed between two portions of tissue using the methods described above (e.g., via a needle, a syringe, or a catheter).

As another example, protective layer 145 can be formed of deionized water and/or a buffered saline solution. The buffered saline solution, for example, can include a composition of saline solution and any of various buffers, such as phosphate. In certain embodiments, the deionized water can similarly include a buffer material, such as phosphate. In some embodiments, the deionized water and/or the buffered saline solution can provide an electrical resistance of about 175 kohms or greater (e.g., about 200 kohms or greater, about 225 kohms or greater, about 250 kohms or greater, about 275 kohms or greater, about 300 kohms or greater, about 325 kohms or greater, about 350 kohms or greater). As used herein, the electrical resistance is tested using ASTM D257-99.

As a further example, in certain embodiments, protective layer 145 can be formed of a combination of one or more of the following: deionized water; a buffered saline solution; particles; liquid polymers; gels; gases and/or foams.

As another example, while certain forms of energy have been described, other forms of energy can be used to treat medical conditions. Examples of forms of energy that can be used include microwave energy, ultrasonic energy, laser energy, and/or heat. Similarly, the unhealthy tissue can be cooled. The energy can be administered to the unhealthy tissue using any of various techniques. For example, a probe can be inserted into the unhealthy tissue and activated to release one or more types of energy.

In some embodiments particles including a relatively conductive material (e.g., a ferromagnetic material) can be disposed within the tissue of the subject to enhance the effects of the energy (e.g., RF energy) transmitted to unhealthy tissue 140. In certain embodiments in which particles including a ferromagnetic material have been disposed within the tissue, a magnetic field can be applied to the particles to affect the extent of conductivity. The magnetic field can be varied to adjust the conductivity of the particles (and, therefore, to adjust the extent of heating and ablation caused by the transmitted energy). In some embodiments, the particles can be used in an agitation ablation process. In such a process, a magnetic field can be used to agitate the particles, such that the particles heat and/or physically deform the surrounding tissue, thereby ablating the surrounding tissue. These and other tissue treatment techniques are described in U.S. Pub. Pat. App. No. US-2004-0101564-A1, which is incorporated herein by reference.

As an additional example, while embodiments have been described in which unhealthy liver tissue is treated, other types of unhealthy tissue can also be treated. Examples of other types of tissue that can be treated include bodily vessel tissue, bone tissue, brain tissue, breast tissue, kidney tissue, liver tissue, lung tissue, ovary tissue, prostate tissue, skin tissue, and thyroid tissue.

As a further example, in some embodiments, energy can be used to treat healthy tissue. In some embodiments, for example, the healthy tissue is undesired tissue. For example, energy can be used to treat (e.g., remove) various types of malformed tissue, such as tissue resulting in webbed fingers and/or toes. As a further example, energy can be used to treat various types of malfunctioning tissue. In embodiments in which healthy tissue is treated with energy, it may be desired, for example, to preserve adjacent regions of healthy tissue. Thus, protective layer 145 can be disposed between two regions of healthy tissue.

The medical treatments described herein can similarly be used to treat various other types of medical conditions. For example, in some embodiments, regions of brain tissue may be treated (e.g., destroyed) with electrical stimulation to treat epilepsy. Similarly, regions of nerve tissue may be treated (e.g., destroyed) to treat chronic pain. In certain embodiments, regions of bodily vessel tissue can be treated to occlude the vessel. This can be beneficial, for example, in treating fibroids (e.g., uterine fibroids), varicose veins, alterior venous malformations, and certain forms of trauma.

Other embodiments are in the claims.

What is claimed is:

1. A method, comprising:
   separating a first portion of tissue of a subject from a second portion of tissue of the subject so that there is a space between the first and second portions of tissue;
   disposing a material between the first and second portions of tissue; and
   exposing the first portion of tissue to energy to treat the first portion of tissue,
   wherein:
      the material is selected from at least one member of the group consisting of deionized water, a buffered saline solution, liquid polymers, gels, particles, foams and gases; and
      the second portion of tissue is substantially unexposed to the energy while the first portion of tissue is exposed to the energy.

2. The method of claim 1, wherein the energy comprises at least one member selected from the group consisting of RF energy, microwave energy, ultrasonic energy, laser energy, and heat.

3. The method of claim 1, wherein exposing the first portion of tissue to energy comprises cooling the first portion of tissue.

4. The method of claim 1, wherein the first portion of tissue comprises an unhealthy tissue.

5. The method of claim 4, wherein the first portion of tissue comprises cancerous tissue.

6. The method of claim 4, wherein the second portion of tissue comprises a healthy tissue.

7. The method of claim 1, wherein the first portion of tissue comprises at least one member of the group consisting of bodily vessel tissue, bladder tissue, bone tissue, brain tissue, breast tissue, bronchi tissue, diaphragm tissue, esophagus tissue, gall bladder tissue, heart tissue, intestine tissue, kidney tissue, larynx tissue, liver tissue, lung tissue, lymph vessel tissue, lymph node tissue, nerve tissue, ovary tissue, pancreas tissue, prostate tissue, skin tissue, stomach tissue, thyroid tissue, trachea tissue, urethra tissue, ureter tissue, uterus tissue, and vertebral disc tissue.

8. The method of claim 1, wherein the second portion of tissue comprises at least one member of the group consisting of bodily vessel tissue, bladder tissue, bone tissue, brain tissue, breast tissue, bronchi tissue, diaphragm tissue, esophagus tissue, gall bladder tissue, heart tissue, intestine tissue, kidney tissue, larynx tissue, liver tissue, lung tissue, lymph vessel tissue, lymph node tissue, nerve tissue, ovary tissue, pancreas tissue, prostate tissue, skin tissue, stomach tissue, and thyroid tissue, trachea tissue, urethra tissue, ureter tissue, uterus tissue, and vertebral disc tissue.

9. The method of claim 1, wherein the first portion of tissue is the same type of tissue as the second portion of tissue.

10. The method of claim 1, wherein the material comprises a liquid polymer.

11. The method of claim 10, wherein the liquid polymer comprises at least one member selected from the group consisting of polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co- glycolic) acids, polypropylene, polytetrafluorethylene, polyethyleneterephthalate, polycarbonate, polyphenyleneoxide, polysulfone, polyhydantoine, polyamide-imide, polyimide, cellulose triacetate, and cellulose acetate butyrate.

12. The method of claim 1, wherein the material comprises a gel.

13. The method of claim 12, wherein the gel comprises at least one member selected from the group consisting of polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co- glycolic) acids, polypropylene, polytetrafluorethylene, polyethyleneterephthalate, polycarbonate, polyphenyleneoxide, polysulfone, polyhydantoine, polyamide-imide, polyimide, cellulose triacetate, and cellulose acetate butyrate.

14. The method of claim 1, wherein the material comprises particles.

15. The method of claim 14, wherein the particles have a size of at most about 10,000 microns.

16. The method of claim 14, wherein the particles comprise at least one material selected from the group consisting of polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co- glycolic) acids, polypropylene, polytetrafluorethylene, polyethyleneterephthalate, polycarbonate, polyphenyleneoxide, polysulfone, polyhydantoine, polyamide-imide, polyimide, cellulose triacetate, and cellulose acetate butyrate.

17. The method of claim 1, wherein the particles comprise a material having a dielectric constant of at least about 2.1.

18. The method of claim 1, wherein the particles comprise a material having a dielectric strength of at least about 100 Kv/mm.

19. The method of claim 1, wherein the material comprises a foam.

20. The method of claim 19, wherein the foam comprises at least one member selected from the group consisting of polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co- glycolic) acids, polypropylene, polytetrafluorethylene, polyethyleneterephthalate, polycarbonate, polyphenyleneoxide, polysulfone, polyhydantoine, polyamide-imide, polyimide, cellulose triacetate, and cellulose acetate butyrate.

21. The method of claim 1, wherein the material comprises a gas.

22. The method of claim 1, wherein the material comprises deionized water.

23. The method of claim 1, wherein the material comprises a buffered saline solution.

24. The method of claim 1, wherein the material comprises at least one member selected from the group consisting of water soluble polysaccharides and ionically cross- linkable polymers.

25. The method of claim 1, wherein the material comprises a ceramic material.

26. The method of claim 1, wherein the material is capable of undergoing an endothermic reaction.

27. The method of claim 1, wherein the space between the first and second portions of tissue is at most about five centimeters.

28. A method, comprising:
separating a first portion of tissue of a subject from a second portion of tissue of the subject so that there is a space between the first and second portions of tissue;
disposing a material between the first and second portions of tissue; and
exposing the first portion of tissue to energy to treat the first portion of tissue,
wherein:
the material is selected from at least one member of the group consisting of deionized water, a buffered saline solution, liquid polymers, gels, particles, foams and gases; and
the second portion of tissue is substantially unexposed to the energy while the first portion of tissue is exposed to the energy, and the space between the first and second portions of tissue is at most about five centimeters.

29. The method of claim 28, wherein the energy comprises at least one member selected from the group consisting of RF energy, microwave energy, ultrasonic energy, laser energy, and heat.

30. The method of claim 28, wherein exposing the first portion of tissue to energy comprises cooling the first portion of tissue.

31. The method of claim 28, wherein the material comprises a liquid polymer.

32. The method of claim 28, wherein the material comprises a gel.

33. The method of claim 28, wherein the material comprises particles.

34. The method of claim 33, wherein the particles have a size of at most about 10,000 microns.

35. The method of claim 28, wherein the material comprises a foam.

36. The method of claim 28, wherein the material comprises a gas.

37. The method of claim 28, wherein the material comprises deionized water.

38. The method of claim 28, wherein the material comprises a buffered saline solution.

39. The method of claim 28, wherein the material comprises at least one member selected from the group consisting of water soluble polysaccharides and ionically cross-linkable polymers.

40. The method of claim 28, wherein the material comprises a ceramic material.

41. The method of claim 28, wherein the material is capable of undergoing an endothermic reaction.

* * * * *